(12) United States Patent
Noh et al.

(10) Patent No.: US 10,700,290 B2
(45) Date of Patent: Jun. 30, 2020

(54) ORGANIC COMPOUND, AND ORGANIC LIGHT-EMITTING DIODE AND ORGANIC LIGHT-EMITTING DIODE DISPLAY DEVICE INCLUDING THE SAME

(71) Applicant: LG DISPLAY CO., LTD., Seoul (KR)

(72) Inventors: Hyo-Jin Noh, Paju-si (KR); Dae-Wi Yoon, Paju-si (KR); Jun-Yun Kim, Goyang-si (KR)

(73) Assignee: LG DISPLAY CO., LTD., Seoul (KR)

( * ) Notice: Subject to any disclaimer, the term of this patent is extended or adjusted under 35 U.S.C. 154(b) by 233 days.

(21) Appl. No.: 15/839,336

(22) Filed: Dec. 12, 2017

(65) Prior Publication Data

US 2018/0166636 A1 Jun. 14, 2018

(30) Foreign Application Priority Data

Dec. 13, 2016 (KR) .................. 10-2016-0169408

(51) Int. Cl.
*H01L 51/50* (2006.01)
*H01L 51/00* (2006.01)
*C09K 11/06* (2006.01)
*C07D 209/82* (2006.01)
*C07D 403/14* (2006.01)
*C07D 401/14* (2006.01)
*C07D 401/10* (2006.01)

(52) U.S. Cl.
CPC ........ *H01L 51/0072* (2013.01); *C07D 209/82* (2013.01); *C07D 401/10* (2013.01); *C07D 401/14* (2013.01); *C07D 403/14* (2013.01); *C09K 11/06* (2013.01); *H01L 51/0059* (2013.01); *H01L 51/0067* (2013.01); *C09K 2211/1007* (2013.01); *C09K 2211/1029* (2013.01); *H01L 51/5012* (2013.01); *H01L 2251/552* (2013.01)

(58) Field of Classification Search
None
See application file for complete search history.

(56) References Cited

U.S. PATENT DOCUMENTS

2008/0001529 A1\* 1/2008 Park .................. H01L 51/5088
313/504

FOREIGN PATENT DOCUMENTS

WO    WO 2014017844    \*  1/2014   ............. H01L 51/50

OTHER PUBLICATIONS

Zhang et al., "Design of Efficient Thermally Activated Delayed Fluorescence Materials for Pure Blue Organic Light Emitting Diodes", J. American Chemical Society, vol. 134 (2012) pp. 14706-14709.

\* cited by examiner

*Primary Examiner* — Gregory D Clark
(74) *Attorney, Agent, or Firm* — Birch, Stewart, Kolasch & Birch, LLP

(57) ABSTRACT

An organic compound is represented by the Formula below, and an organic light-emitting diode and an organic light-emitting diode display device include the organic compound.

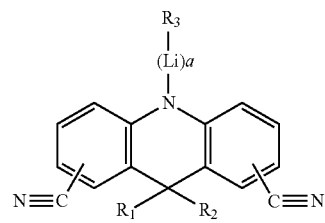

14 Claims, 3 Drawing Sheets

ORGANIC COMPOUND, AND ORGANIC LIGHT-EMITTING DIODE AND ORGANIC LIGHT-EMITTING DIODE DISPLAY DEVICE INCLUDING THE SAME

CROSS-REFERENCE TO RELATED APPLICATIONS

This application claims the priority benefit under 35 U.S.C. § 119(a) of Korean Patent Application No. 10-2016-0169408, filed on Dec. 13, 2016, in the Korean Intellectual Property Office, which is incorporated herein by reference in its entirety into the present application.

BACKGROUND

Field of the Disclosure

The present disclosure relates to an organic compound, and more particularly, to an organic compound applicable to an organic layer of an organic light-emitting diode, and an organic light-emitting diode and an organic light-emitting diode display device including the same.

Discussion of the Related Art

An organic light-emitting diode (OLED), also called an organic electroluminescent device (OELD), is a widely used flat display device. Technology for fabricating the OLED is rapidly developing.

An OLED is formed of organic thin films having a thickness of 2,000 Å or less. An OLED produces images in one or both directions depending on the configuration of electrodes used. Further, in an organic light-emitting diode display device, an element can be formed on a flexible transparent substrate such as a plastic substrate, so that a flexible or foldable display device can be obtained. In addition, an organic light-emitting diode display device has significant advantages over a liquid crystal display (LCD) device. For example, the organic light-emitting diode display device can be driven at a low voltage and has excellent color purity.

An OLED includes a hole injection electrode (anode), an electron injection electrode (cathode), and an organic light-emitting layer formed between the anode and the cathode. To increase luminous efficacy, an organic light-emitting layer may include a hole injection layer, a hole transport layer, a light-emitting material layer, an electron transport layer, and an electron injection layer sequentially stacked on a hole injection electrode. In this case, holes injected from an anode and electrons injected from a cathode combine in a light-emitting material layer to form excitons resulting in an unstable excited state. At this time, the excited state returns to a stable ground state, and light is emitted. The external quantum efficiency (EQE; $\eta_{ext}$) of a light-emitting material applied to a light-emitting material layer is calculated by the following equation (Equation 1).

$$\eta_{ext} = \eta_{int} \times \Gamma \times \Phi \times \eta_{out\text{-}coupling}$$

($\eta_{int}$ refers to internal quantum efficiency (IQE); $\Gamma$ refers to a charge balance factor; $\Phi$ refers to radiative quantum efficiency; and $\eta_{out\text{-}coupling}$ refers to light out-coupling efficiency)

The internal quantum efficiency ($\eta_{int}$) represents the ratio of excitons converted into light to all excitons generated. For fluorescent materials, the internal quantum efficiency is limited to a maximum of 0.25. Theoretically, when holes and electrons meet to form excitons, single excitons in a paired spin state and triplet excitons in an unpaired spin state are generated in a ratio of 1:3 depending on spin configurations. In the case of fluorescent materials, only singlet excitons participate in light emission and the remaining 75%, triplet excitons do not participate in light emission. Thus, the internal quantum efficiency of fluorescent materials is low.

Charge balance factor ($\Gamma$) means the balance between holes and electrons forming excitons and generally has a value of 1 assuming that holes and electrons are 100% matched (i.e., 1:1 matched). Radiative quantum efficiency ($\Phi$) is a substantial value related to the luminous efficacy of a light-emitting material and depends on the photoluminescence (PL) of the dopant of a host-dopant system.

Light out-coupling efficiency ($\eta_{out\text{-}coupling}$) represents the ratio of light extracted outward from a light-emitting material to total light emitted from the light-emitting material. In general, when a thin film is formed by thermal vapor deposition of an isotropic light-emitting material, each luminescent molecule does not have a particular directionality and is present in a disordered state. The light out-coupling efficiency in such a random orientation state is generally assumed to be 0.2.

Therefore, when the four components shown in Equation 1 are combined, the maximum luminous efficacy of the organic light-emitting diode using a fluorescent material is only about 5%. Thus, to solve the low efficiency of fluorescent materials, phosphorescent materials with a light-emitting mechanism in which both singlet energy and triplet energy are converted into light have been developed.

However, metal complex compounds generally used as phosphorescent materials are expensive and have a short lifespan, and thus are limited in commercialization. In particular, blue phosphorescent materials fail to meet the luminous efficacy and reliability required in the industry.

Therefore, there is a demand for the development of a light-emitting material, which has high reliability, excellent luminous efficacy, and improves the lifespan of a device.

SUMMARY

Therefore, the present disclosure has been made in view of the above problems. It is an objective of the present disclosure to provide an organic compound having excellent luminous efficacy and color purity, and an organic light-emitting diode and an organic light-emitting diode display device having an improved lifespan using the organic compound.

In accordance with an embodiment of present disclosure, the above and other objectives can be accomplished by the provision of an organic compound having an acridine moiety containing two cyanide groups.

The organic compound is represented by Formula 1 below:

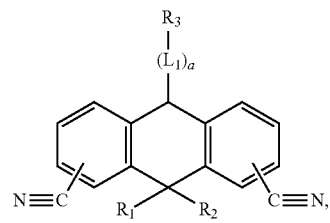

Formula 1 wherein each of $R_1$ to $R_3$ is independently selected from a group comprising an unsubstituted or substituted C1 to C20 alkyl group, an unsubstituted or substituted C1 to C20 alkoxy group, an unsubstituted or substituted C3 to C30 cycloalkyl group, an unsubstituted or substituted C3 to C30 heterocycloalkyl group, an unsubstituted or substituted C5 to C30 aryl group and an unsubstituted or substituted C4 to C30 heteroaryl group, and $L_1$ is selected from a group comprising an unsubstituted or substituted C1 to C20 alkylene group, an unsubstituted or substituted C1 to C20 alkoxylene group, an unsubstituted or substituted C3 to C30 cycloalkylene group, an unsubstituted or substituted C3 to C30 heterocycloalkylene group, an unsubstituted or substituted C5 to C30 arylene group and an unsubstituted or substituted C4 to C30 heteroarylene group, and wherein "a" is 0 or 1.

In accordance with an aspect of the present disclosure, the above and other objectives can be accomplished by the provision of an organic light-emitting diode and an organic light-emitting diode display device, in which the above-described organic compound is applied to an organic light-emitting layer.

The organic compound may be used as the host of the light-emitting material layer.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
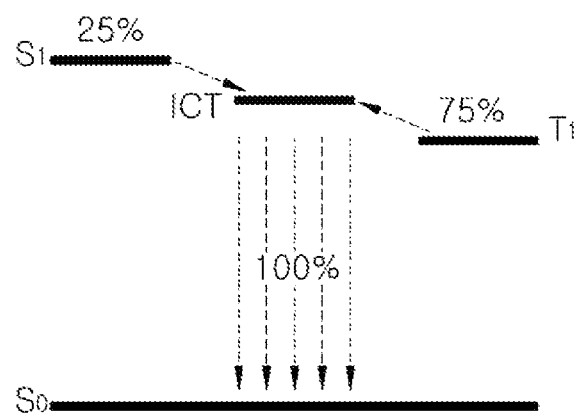
FIG. 1 is a schematic diagram for describing the luminescent mechanism of a delayed fluorescence compound used with the organic compound according to one exemplary embodiment of the present disclosure.

Hereinafter, the present disclosure is described in more detail with reference to the accompanying drawings.

[Organic Compound]

The organic compound according to an aspect of the present disclosure has a structure in which two cyanide groups (CNs) are connected to an acridine moiety and other substituents are connected to the acridine moiety through linkers. The organic compound according to an aspect of the present disclosure may be represented by Formula 1 below:

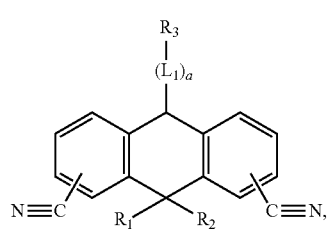

Formula 1 wherein each of $R_1$ to $R_3$ is independently selected from a group comprising an unsubstituted or substituted C1 to C20 alkyl group, an unsubstituted or substituted C1 to C20 alkoxy group, an unsubstituted or substituted C3 to C30 cycloalkyl group, an unsubstituted or substituted C3 to C30 heterocycloalkyl group, an unsubstituted or substituted C5 to C30 aryl group and an unsubstituted or substituted C4 to C30 heteroaryl group, and $L_1$ represents an unsubstituted or substituted C1 to C20 alkylene group, an unsubstituted or substituted C1 to C20 alkoxylene group, an unsubstituted or substituted C3 to C30 cycloalkylene group, an unsubstituted or substituted C3 to C30 heterocycloalkylene group, an unsubstituted or substituted C5 to C30 arylene group or an unsubstituted or substituted C4 to C30 heteroarylene group. "a" is 0 or 1.

As used herein, the term "unsubstituted" or "substituted" indicates that a hydrogen atom is unsubstituted or substituted, in which case the hydrogen atom includes protium, deuterium, or tritium.

Examples of substituents used in this specification include a C1 to C20 alkyl group in which a hydrogen atom is unsubstituted or substituted by a halogen, a C1 to C20 alkoxy group in which a hydrogen atom is unsubstituted or substituted by a halogen, a cyano group, —CF3, a hydroxyl group, a carboxyl group, a carbonyl group, an amine group, a C1 to C10 alkyl-substituted amine group, a C5 to C30 aryl-substituted amine group, a C4 to C30 heteroaryl-substituted amine group, a nitro group, a hydrazyl group, a sulfonic acid group, a C1 to C20 alkylsilyl group, a C1 to C20 alkoxysilyl group, a C3 to C30 cycloalkylsilyl group, a C5 to C30 arylsilyl group, a C4 to C30 heteroarylsilyl group, a C5 to C30 aryl group, a C4 to C30 heteroaryl group, and the like, without being limited thereto.

As used herein, the term "hetero", as used in "heteroaromatic ring", "heterocycloalkylene group", "heteroarylene group", "heteroarylalkylalkylene group", "heteroaryloxylene group", "heterocycloalkyl group", "heteroaryl group", "heteroarylalkyl group", "heteroaryloxyl group", "heteroaryl amine group", and the like, indicates that one or more carbon atoms (e.g., 1 to 5 carbon atoms) of carbon atoms constituting these aromatic or alicyclic rings are substituted with one or more heteroatoms selected from the group consisting of N, O, S, and combinations thereof.

For example, when $R_1$ to $R_3$ in Formula 1 are substituted with alkyl groups, the alkyl groups may be linear or branched C1 to C20, preferably C1 to C10 alkyl groups. In addition, when $R_1$ to $R_3$ in Formula 1 are aromatic substituents, the aromatic substituents may be each independently an unsubstituted or substituted phenyl group, a biphenyl group, a terphenyl group, a naphthyl group, a anthracenyl group, a pentanenyl group, an indenyl group, an indenoindenyl group, a heptalenyl group, a biphenylenyl group, an indacenyl group, a phenalenyl group, a phenanthrenyl group, a benzophenanthrenyl group, a dibenzophenanthrenyl group, an azulenyl group, a pyrenyl group, a fluoranthenyl group, a triphenylenyl group, a chrysenyl group, a tetraphenyl group, a tetracenyl group, a pycenyl group, a pentaphenyl group, a pentacenyl group, a fluorenyl group, an indenofluorenyl group or an unfused or fused homoaryl group such as a spiro fluorenyl group, and/or a pyrrolyl group, a pyridinyl group, a pyrimidinyl group, a pyrazinyl group, a pyridazinyl group, a triazinyl group, a tetrazinyl group, an imidazolyl group, a pyrazolyl group, an indolyl group, an isoindolyl group, an indazolyl group, an indolizinyl group, a pyrrolidinyl group, a carbazolyl group, a benzocarbazolyl group, a dibenzocarbazolyl group, an indolocarbazolyl group, an indenocarbazolyl group, a benzofurocarbazolyl group, a benzothienocarbazolyl group, a quinolinyl group, an isoquinolinyl group, a phthalazinyl group, a quinoxalinyl group, a cinolinyl group, a quinazolinyl group, a quinozolinyl group, a quinolizinyl group, a purinyl group, a phthalazinyl group, a quinoxalinyl group, a benzoquinolinyl group, a benzoisoquinolinyl group, a benzoquinazolinyl group, a benzoquinoxalinyl group, an acridinyl group, a phenanthrolinyl group, a perimidinyl group, a phenanthridinyl group, a pteridinyl group, a cinnolinyl group, a naphtharidinyl group, a furanyl group, a pyrenyl group, an oxazinyl group, an oxazolyl group, an oxadiazolyl group, a triazolyl group, a dioxinyl group, a benzofuranyl group, a dibenzofuranyl group, a thiopyrenyl group, a zanthenyl group, a chromenyl group, an isochromenyl group, a thioazinyl group, a thiophenyl group, a benzothiophenyl group, a dibenzothiophenyl group, a difluoropyrazinyl group, a benzofluorodibenzofuranyl group, a benzothienobenzothiophenyl group, a benzothienodibenzothiophenyl group, a benzothienobenzofuranyl group, a benzothienodibenzofuranyl group or an unfused or fused heteroaryl group such as an N-substituted spirofluorenyl group.

Meanwhile, in one non-limiting embodiment, in Formula 1, $L_1$, which is a linker, may be a linear or branched C1 to C20, preferably a C1 to C10 alkylene group. In another exemplary embodiment, L1 may be an aromatic linker.

More specifically, in Formula 1, $L_1$ may be selected from the group consisting of a substituted or unsubstituted phenylene group, a biphenylene group, a terphenylene group, a tetraphenylene group, an indenylene group, a naphthylene group, an azulenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a benzoquinolinylene group, a benzoisoquinolinylene group, a benzoquinazolinylene group, a benzoquinoxalinylene group, a cinnolinylene group, a phenanthridinylene group, an acridinylene group, a phenanthrolinylene group, a phenazinylene group, a benzoxazolylene group, a benzimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a benzofuranylene group, a dibenzofuranylene group, a benzofluodibenzofuranylene group, a benzothienobenzofuranylene group, a benzothienodibenzofuranylene group, a benzothiophenylene group, a dibenzothiophenylene group, a benzothietobenzothiophenylene group, a benzothienodibenzothiophenylene group, a carbazolylene group, a benzocarbazolylene group, a dibenzocarbazolylene group, an indolocarbazolylene group, an indenocarbazolylene group, a benzofurocarbazolylene group, a benzothienocarbazolylene group, an imidazopyrimidinylene group, and an imidazopyridinylene group.

In one exemplary embodiment, when the number of aromatic rings constituting $L_1$ is increased, the conjugated structure of an entire organic compound becomes excessively long, so that the energy band gap of the organic compound may be excessively reduced. Accordingly, the number of aromatic rings constituting $L_1$ is preferably 1 to 2, more preferably 1. In addition, with respect to the injection and transport properties of holes, $L_1$ may be a 5-membered ring to a 7-membered ring, preferably a 6-membered ring. For example, $L_1$ may be a substituted or unsubstituted phenylene group, a biphenylene group, a pyrrolylene group, an imidazolylene group, a pyrazolylene group, a pyridinylene group, a pyrazylene group, a pyrimidinylene group, a pyridazinylene group, a furanylene group or a thiophenylene group.

The organic compound represented by Formula 1 has an acridine moiety capable of functioning as an electron donor. A cyanide group is connected to each of aromatic rings disposed on both sides of the acridine moiety, and other substituents are connected to the moiety through linkers. When the acridine moiety forms a chemical bond with another moiety, conformational distortion of the acridine moiety becomes large, so that the three-dimensional conformation of the organic compound represented by Formula 1 is restricted. Further, since the compound has cyanide groups, the triplet energy of the compound is not lowered, and a blue shift is facilitated. Therefore, the organic compound according to the present disclosure may be used as the host of an organic light-emitting layer constituting an organic light-emitting diode. In particular, the organic compound may be applied to a light-emitting material layer using a so-called delayed fluorescence compound as a dopant, which is described below.

FIG. 1 is a schematic diagram for describing the luminescent mechanism of a delayed fluorescence compound used with the organic compound according to one exemplary embodiment of the present disclosure. Delayed fluorescence may be classified as thermally activated delayed fluorescence (TADF) and field activated delayed fluorescence (FADF). Triplet excitons are activated by heat or an electric field so that so-called super-fluorescence exceeding the maximum luminous efficacy of conventional fluorescent materials may be realized.

That is, in a delayed fluorescence compound, triplet excitons are activated by heat or an electric field generated when a device is driven, and the activated triplet excitons are involved in light emission. In general, a delayed fluorescence compound has both an electron donor moiety and an electron acceptor moiety so that the delayed fluorescence compound is capable of being in an intramolecular charge transfer (ICT) state. When a delayed fluorescence compound capable of being in an ICT state is used as a dopant, in the delayed florescent compound, excitons having a singlet energy level ($S_1$) and excitons having a triplet energy level ($T_1$) move to an ICT state, an intermediate state, ($S_1 \rightarrow ICT \leftarrow T_1$) and then a transition to a ground state (S0) occurs. Both the exciton having a singlet energy level ($S_1$) and the exciton having a triplet energy level ($T_1$) participate in luminescence, so that internal quantum efficiency may be improved, and thus luminous efficacy may be improved.

In the case of conventional fluorescent materials, since the highest occupied molecular orbital (HOMO) and the lowest unoccupied molecular orbital (LUMO) are distributed throughout a molecule, it is impossible to switch between a singlet state and a triplet state (selection rule). However, since a compound having an ICT state has a small overlap between the HOMO and the LUMO, the interaction between the HOMO and the LUMO is small. Accordingly, the change of the spin state of electrons does not affect other electrons, and a new charge transfer band (CT band) not conforming to the selection rule is formed.

That is, since an electron acceptor moiety and an electron donor moiety are spaced apart in a delayed fluorescence compound, an intramolecular dipole moment is present in a highly polarized state. When a dipole moment is polarized, the interaction between the orbit of the HOMO state and the orbit of the LUMO state is reduced, a transition from a triplet state or a singlet state to an intermediate state (i.e., ICT) becomes possible, and excitons having a triplet energy level ($T_1$) as well as excitons having a singlet energy level ($S_1$) participate in luminescence. That is, when a light-emitting device is driven, excitons having a singlet energy level ($S_1$) of 25% and excitons having a triplet energy level ($T_1$) of 75% are shifted to an intermediate state (ICT) by heat or an electric field, and then a transition to a ground state (S0) occurs and light is emitted. Thus, internal quantum efficiency is theoretically 100%.

A dopant and a host for implementing delayed fluorescence should have the following characteristics. A dopant should have an electron donor moiety and an electron acceptor moiety at the same time in one molecule to implement intramolecular charge transfer (ICT). A dopant usually has the form of an ICT complex, in which an electron donor moiety and an electron acceptor moiety are present in one molecule, so that electron transfer within the molecule easily occurs. That is, in an ICT complex under certain conditions, one electron in an electron donor moiety migrates to an electron acceptor portion, resulting in charge separation in a molecule. In addition, in order for energy transition to occur in both triplet and singlet states, in a dopant for implementing delayed fluorescence, the difference between a singlet energy level ($S_1$) and a triplet energy level ($T_1$) should be 0.3 eV or less, for example, 0.05 to 0.3 eV.

Figure 2:
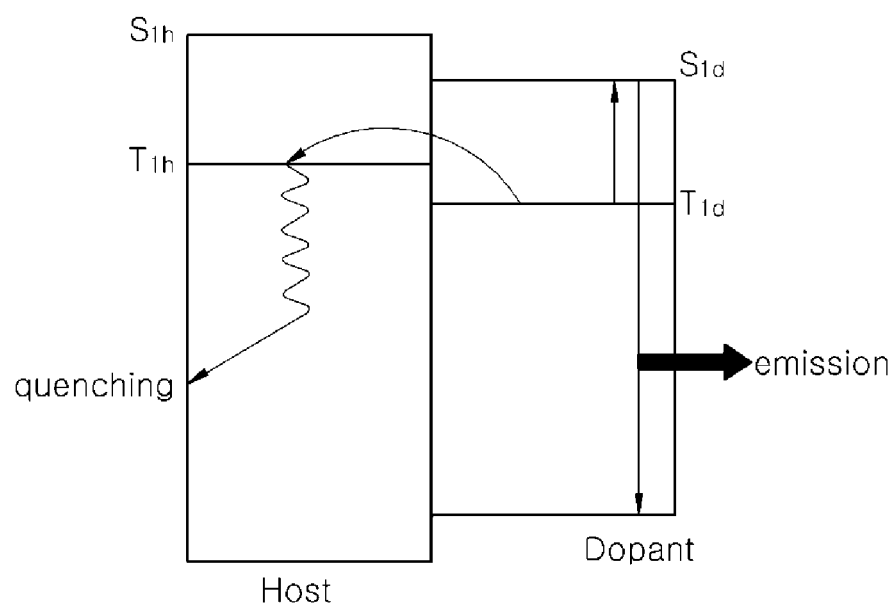
FIG. 2 is a schematic diagram for describing energy level changes occurring between the organic compound according to one exemplary embodiment of the present disclosure and a delayed fluorescence compound when the organic compound is used as a host.

In addition, a host for implementing delayed fluorescence should be able to induce excitons in a triplet state in a dopant to participate in luminescence without being quenched (non-emitting extinction). FIG. 2 is a schematic diagram for describing energy levels between the organic compound according to one exemplary embodiment of the present disclosure and a delayed fluorescence compound when the organic compound is used as a host.

As shown in FIG. 2, the energy levels between a host and a dopant for implementing delayed fluorescence should be adjustable. First, the triplet energy level ($T_{1h}$) of the host should be higher than the triplet energy level ($T_{1d}$) of the dopant. When the triplet energy level ($T_{1h}$) of the host is not sufficiently higher than the triplet energy level ($T_{1d}$) of the dopant, the triplet-state excitons of the dopant are passed to the triplet energy level ($T_{1h}$) of the host, and disappear through non-emitting extinction (quenching), so that the triplet-state excitons of the dopant do not contribute to luminescence.

In addition, it is necessary to appropriately adjust the HOMO energy level and the LUMO energy level of a host and a dopant. For example, the difference ($|HOMO_{Host}-HOMO_{Dopant}|$) between the highest occupied molecular orbital energy level of a host ($HOMO_{Host}$) and the highest occupied molecular orbital energy level of a dopant ($HOMO_{Dopant}$) or the difference ($|LUMO_{Host}-LUMO_{Dopant}|$) between the lowest unoccupied molecular orbital energy level of a host ($LUMO_{Host}$) and the lowest unoccupied molecular orbital energy level of a dopant ($LUMO_{Dopant}$) is preferably 0.5 eV or less, for example, 0.1 to 0.5 eV or less. As a result, charge transfer efficiency from the host to the dopant is improved, and luminous efficacy may thus be improved. In addition, to secure a long device lifespan, the host should have a rigid structure.

The organic compound represented by Formula 1 has an acridine moiety. When the acridine moiety forms a chemical bond with another moiety, conformational distortion of the acridine moiety becomes large. Thus, steric hindrance increases between the acridine moiety and adjacent moieties. The organic compound represented by Formula 1 is structurally robust because the number of three-dimensional conformations which a molecule may have is minimized. Since the number of three-dimensional conformations is limited and an emission spectrum may be limited to a specific range, high color purity may be realized. In addition, since cyanide groups having excellent characteristics as an electron-attractor are introduced into both side rings constituting the acridine moiety, a blue shift may be realized without lowering a triplet state energy level ($T_{1h}$).

In one exemplary embodiment, the organic compound according to the present disclosure includes a compound represented by Formula 2 below:

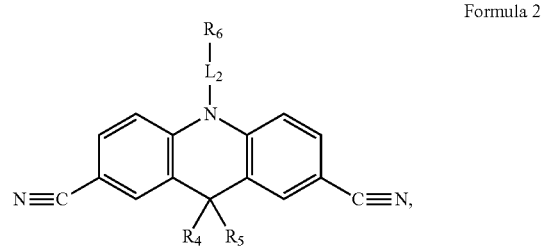

Formula 2 wherein each of $R_4$ and $R_5$ is independently selected from a group comprising an unsubstituted or substituted C1 to C20 alkyl group, an unsubstituted or substituted C5 to C30 aryl group or an unsubstituted or substituted C4 to C30 heteroaryl group; $R_6$ is selected from a group comprising an unsubstituted or substituted C5 to C30 aryl group and an unsubstituted or substituted C4 to C30 heteroaryl group. $L_2$ is selected from a group comprising an unsubstituted or substituted C5 to C10 arylene group consisting of one or two rings and an unsubstituted or substituted C4 to C30 heteroarylene group consisting of one or two rings.

More specifically, the organic compound according to the present disclosure may be any one of compounds represented by Compounds 1 to 14 below:

Compound 1
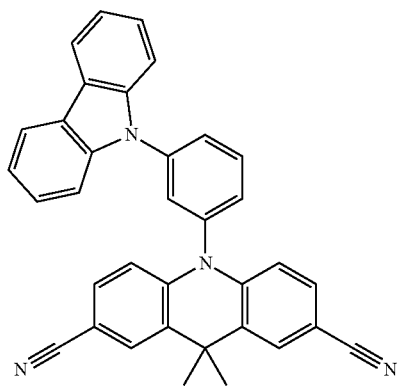
Compound 2
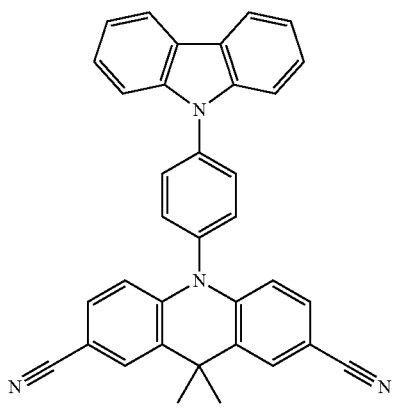
Compound 3
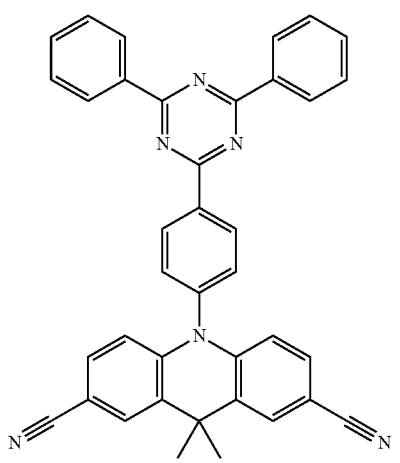
Compound 4
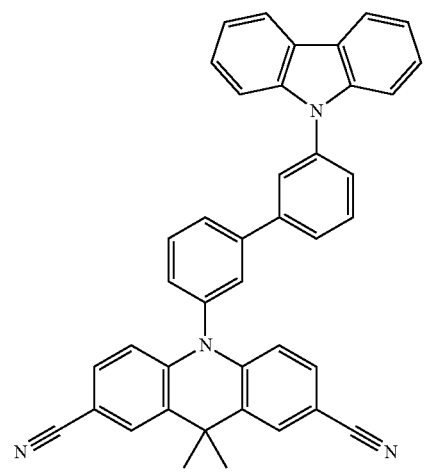
Compound 5
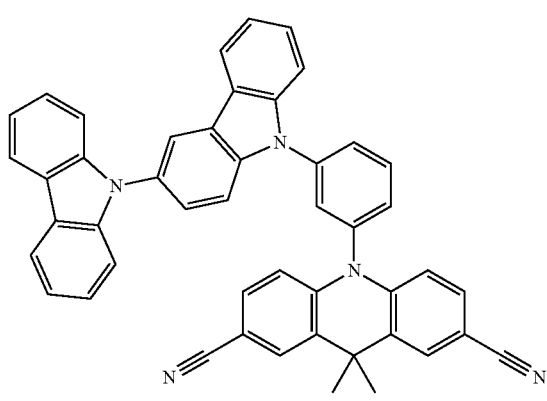
Compound 6
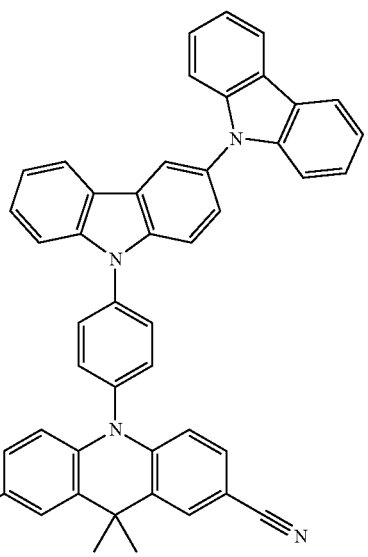

Compound 7
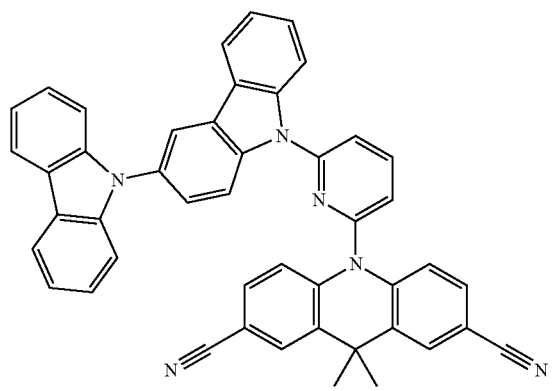
Compound 8
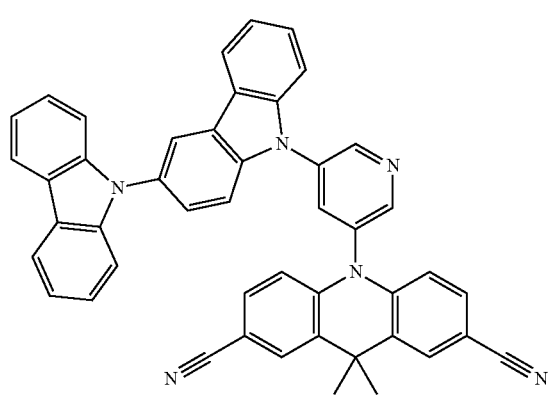
Compound 9
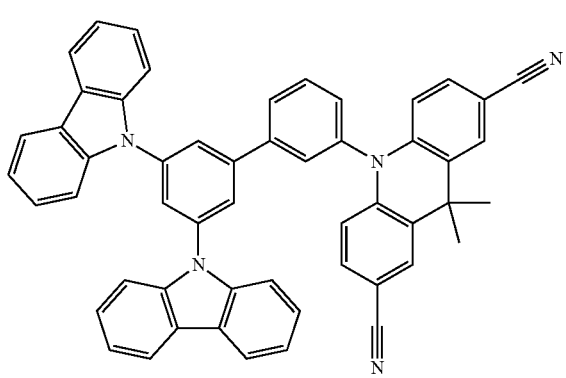
Compound 10
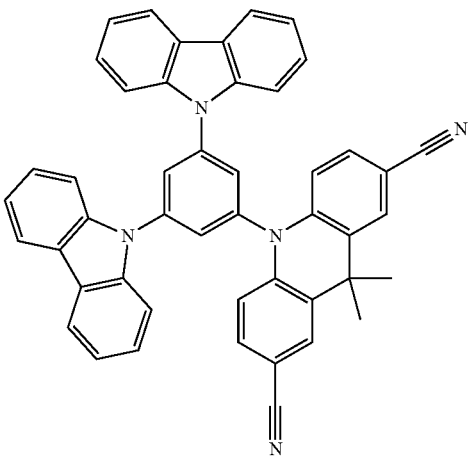
Compound 11
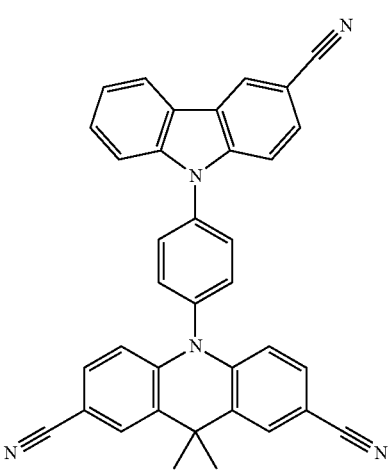
Compound 12
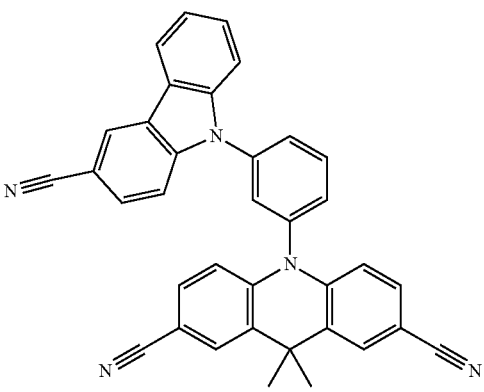

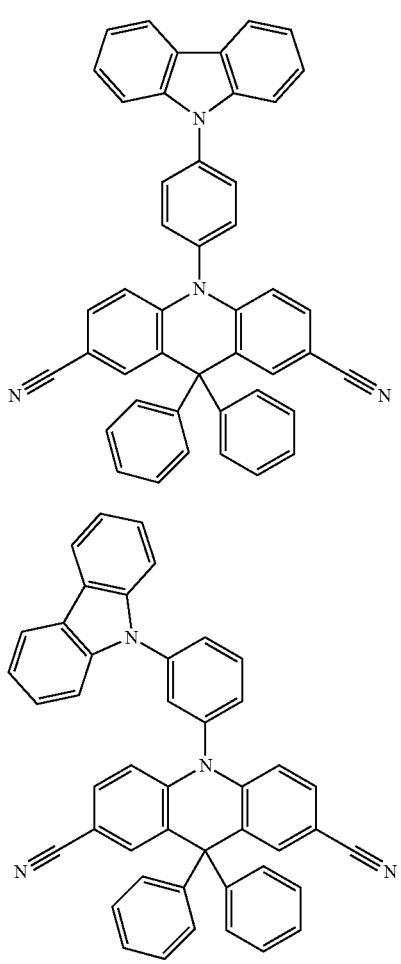

Compound 13

Compound 14

When the organic compound represented by Formula 2 or any of Compounds 1 to 14 combines with another moiety, steric hindrance occurs. However, the organic compound is structurally robust because the compound has an acridine moiety in which a three-dimensional conformation is limited. Accordingly, when the organic compound of the present disclosure having a limited three-dimensional conformation is used as a light-emitting material, excellent color purity may be secured and energy may be efficiently transferred to a dopant without losing energy in a light emission process. In addition, a cyanide group is connected to each of both side rings of the acridine moiety so that a triplet energy level is not lowered and a blue shift is facilitated. Since energy may be efficiently transferred to a dopant, the luminous efficacy of a light-emitting device to which the organic compound of the present disclosure is applied may be improved and the lifespan of the light-emitting device may be extended.

[Organic Light-Emitting Diode and Organic Light-Emitting Diode Display Device]

Figure 3:
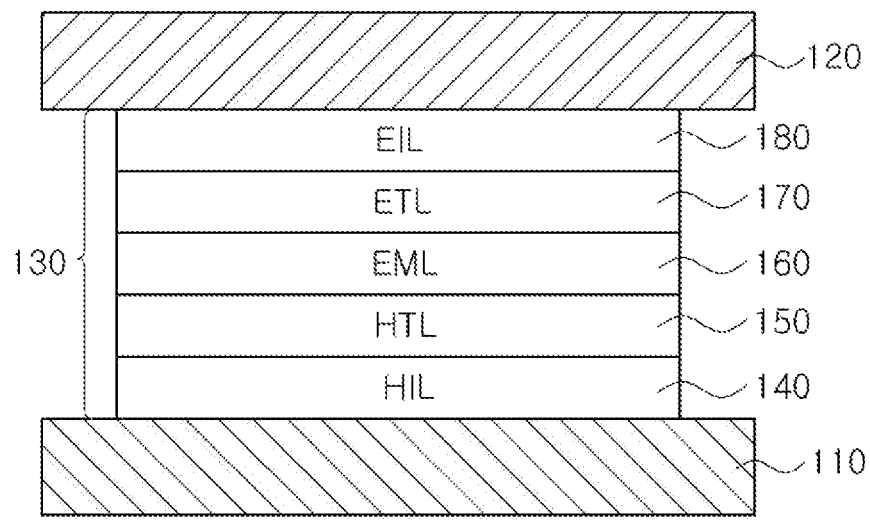
FIG. 3 is a cross-sectional view schematically showing an organic light-emitting diode in which an organic compound is applied to an organic light-emitting layer according to one exemplary embodiment of the present disclosure.

As described above, since organic compounds represented by Formulas 1 to 2 and any one of Compounds 1 to 14 are used as a light-emitting material in an organic light-emitting layer constituting an organic light-emitting diode, it is possible to realize a light-emitting device having excellent color purity, improved luminous efficacy and an increased element lifespan. This is described in detail below. FIG. 3 is a cross-sectional view schematically showing an organic light-emitting diode in which an organic compound is applied to an organic light-emitting layer according to one exemplary embodiment of the present disclosure.

As shown in FIG. 3, according to the first embodiment of the disclosure, an organic light-emitting diode 100 includes a first electrode 110 and a second electrode 120 facing each other and an organic light-emitting layer 130 disposed between the first and second electrodes 110 and 120. In one exemplary embodiment, the organic light-emitting layer 130 includes a hole injection layer (HIL) 140, a hole transport layer (HTL) 150, a light-emitting material layer (EML) 160, an electron transport layer (ETL) 170, and an electron injection layer (EIL) 180, which are sequentially stacked from the first electrode 110.

The first electrode 110 may be an anode for supplying holes to the light-emitting material layer 160. The first electrode 110 is preferably formed of a conductive material having a relatively large work function value, for example, a transparent conductive oxide (TCO). For example, the first electrode 110 may be formed of indium-tin-oxide (ITO), indium-zinc-oxide (IZO), indium-tin-zinc oxide (ITZO), tin oxide (SnO), zinc oxide (ZnO), indium-copper-oxide (ICO), and aluminum zinc oxide (Al:ZnO; AZO).

The second electrode 120 may be a cathode for supplying electrons to the light-emitting material layer 160. The second electrode 120 may be formed of conductive materials having a relatively low work function value and having excellent reflective properties such as aluminum (Al), magnesium (Mg), calcium (Ca), silver (Ag), or alloys or combinations thereof.

A hole injection layer 140 is disposed between the first electrode 110 and the hole transport layer 150 and improves interface characteristics between the first electrode 110, an inorganic material, and the hole transport layer 150, an organic material. In one exemplary embodiment, the hole injection layer 140 may be formed of any one of compounds such as (4,4',4"-tris (3-methylphenylamino)triphenylamine (MTDATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB; NPD), 1,4,5,8,9,11-hexaazatriphenylenehexacarbonitrile (HAT-CN), 1,3,5-tris[4-(diphenylamino)phenyl]benzene (TDAPB), poly (3,4-ethylenedioxythiophene)polystyrene sulfonate (PEDOT/PSS), and/or N-(biphenyl-4-yl)-9,9-dimethyl-N-(4-(9-phenyl-9H-carbazol-3-yl)phenyl)-9H-fluoren-2-amine). The hole injection layer 140 may be omitted depending on the characteristics of the organic light-emitting diode 100.

The hole transport layer 150 is disposed between the first electrode 110 and the light-emitting material layer 160, and adjacent to the light-emitting material layer 160. In one exemplary embodiment, the hole transport layer 150 may be formed of compounds such as N,N'-diphenyl-N,N'-bis(3-methylphenyl)-1,1'-biphenyl-4,4'-diamine (TPD), NPD, 4,4'-bis(N-carbazolyl)-1,1'-biphenyl (CBP), N-(biphenyl-4-yl)-9,9-dimethyl-N-(4-(9-phenyl-9H-carbazol-3-yl)phenyl)-9H-fluoren-2-amine, and/or N- (biphenyl-4-yl)-N-(4-(9-phenyl-9H-carbazol-3-yl)phenyl)biphenyl-4-amine), without being limited thereto.

The light-emitting material layer 160 may be formed by doping a host with a dopant. For example, when the light-emitting material layer 160 is formed, about 1 to 30% by weight of the dopant may be added to the host, and the light-emitting material layer 160 may emit blue light.

The organic compounds represented by Formulas 1, 2 and Compounds 1 to 14 may be used as the host of the light-emitting material layer 160. Meanwhile, a dopant used in the light-emitting material layer 160 may have delayed fluorescence properties.

As described above, compounds with delayed fluorescence properties are activated by heat or an electric field and have an intermediate energy state such as an ICT complex state. Since both an exciton having a singlet energy level and an exciton having a triplet energy level participate in light emission, the luminous efficacy of the organic light-emitting diode 100 may be improved. In addition, the difference ($\Delta E_{ST}$) between the singlet energy level ($S_1$) and the triplet energy level ($T_1$) of the dopant is 0.3 eV or less, these energy levels move to an intermediate state, and then fall to a ground state, whereby the quantum efficiency of the dopant may be improved. That is, the smaller $\Delta E_{ST}$ is, the more the luminous efficacy may be increased. When the difference between the singlet energy level ($S_1$) and the triplet energy level ($T_1$) of the dopant is 0.3 eV or less, singlet state excitons and triplet state excitons may move to an ICT complex state, an intermediate state, by heat or electric field.

In addition, to maximize luminous efficacy due to delayed fluorescence, the triplet energy levels ($T_{1h}$, see FIG. 2) of the organic compounds represented by Formulas 1, 2 and Compounds 1-14 used as a host should be higher than the triplet energy level ($T_{1d}$, see FIG. 2) of a delayed fluorescence compound used as a dopant. In particular, when the difference ($|HOMO_{Host}-HOMO_{Dopant}|$) between the highest occupied molecular orbital energy level of a host ($HOMO_{Host}$) and the highest occupied molecular orbital energy level of a dopant ($HOMO_{Dopant}$) or the difference ($|LUMO_{Host}-LUMO_{Dopant}|$) between the lowest unoccupied molecular orbital energy level of a host ($LUMO_{Host}$) and the lowest unoccupied molecular orbital energy level of a dopant ($LUMO_{Dopant}$) is 0.5 eV or less, energy may be efficiently transferred from the host to the dopant and luminous efficacy may be maximized.

According to one exemplary embodiment, when the organic compound represented by Formula 1 is used as a host, a dopant that shows delayed fluorescence properties and exhibits a proper energy level difference with the host is preferably used. For example, a material used as the dopant of the light-emitting material layer 160 according to the present disclosure may be represented by Formula 3 below, but the present disclosure is not limited thereto.

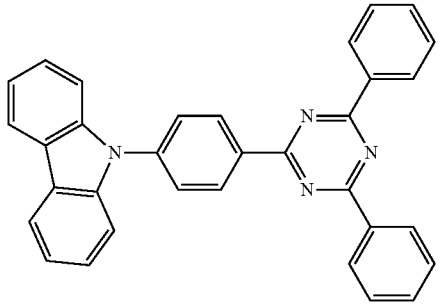

Formula 3

The electron transport layer 170 and the electron injection layer 180 may be sequentially stacked between the light-emitting material layer 160 and the second electrode 120. A material forming the electron transport layer 170 is required to have high electron mobility, and a material satisfying this requirement smoothly and stably transfers electrons to the light-emitting material layer 160.

In one exemplary embodiment, the electron transport layer 170 may be a derivative such as oxadiazole, triazole, phenanthroline, benzoxazole, benzothiazole, benzimidazole, triazine, and the like.

For example, the electron transport layer 170 may be formed of tris-(8-hydroxyquinoline)aluminum (Alq3), 2-biphenyl-4-yl-5-(4-t-butylphenyl)-1,3,4-oxadiazole (PBD), spiro-PBD, lithium quinolate (Liq), 2-[4-(9,10-di-2-naphthalenyl-2-anthracenyl)phenyl]-1-phenyl-1H-benzimidazole, bis(2-methyl-8-quinolinolato-N1,O8)- (1,1'-biphenyl-4-olato)aluminum (BAlq), 3-(biphenyl-4-yl)-5-(4-terbutylphenyl)-4-phenyl-4H-1,2,4-triazole (TAZ), 4,7-diphenyl-1,10-phenanthroline (Bphen), tris (phenylquinoxaline) (TPQ), and/or 1,3,5-tris(N-phenylbenzimiazole-2-yl)benzene (TPBi), without being limited thereto.

The electron injection layer 180 is disposed between the second electrode 120 and the electron transport layer 170. The lifespan of a device may be increased by the electron injection layer 180. In one exemplary embodiment, examples of the material of the electron injection layer 180 may include alkali halides such as LiF, CsF, NaF, and BaF2 and/or organometallic materials such as lithium quinolate (Liq), lithium benzoate, and sodium stearate, without being limited thereto.

The organic light-emitting diode 100 according to an exemplary embodiment of the present disclosure has a dopant having delayed fluorescence properties in the light-emitting material layer 160 constituting the organic light-emitting layer 130. Since excitons in a singlet energy state and a triplet energy state all participate in light emission, luminescence efficiency is improved. In addition, the light-emitting material layer 160 includes a host formed of an organic compound represented by Formula 1, 2 or Compounds 1 to 14.

When the organic compounds represented by Formulas 1, 2 and Compounds 1 to 14 combine with another moiety, distortion is increased, causing steric hindrance. Each of the organic compounds has an acridine moiety capable of functioning as an electron donor. The three-dimensional conformations of the organic compounds represented by Formulas 1, 2 and Compounds 1 to 14 are limited and structurally robust. When the organic compounds represented by Formulas 1, 2 and Compounds 1 to 14 are used as the host of a light-emitting material layer, excellent color purity may be secured, the lifespan of a device may be improved, and energy may be efficiently transferred to a dopant. Since cyanide groups are connected to the acridine moiety, a triplet energy level is not lowered and a blue shift is facilitated. Therefore, when the organic compounds represented by Formulas 1, 2 and Compounds 1 to 14 are used, the organic light-emitting diode 100 having improved luminous efficacy, excellent color purity, and an increased element lifespan may be fabricated.

Figure 4:
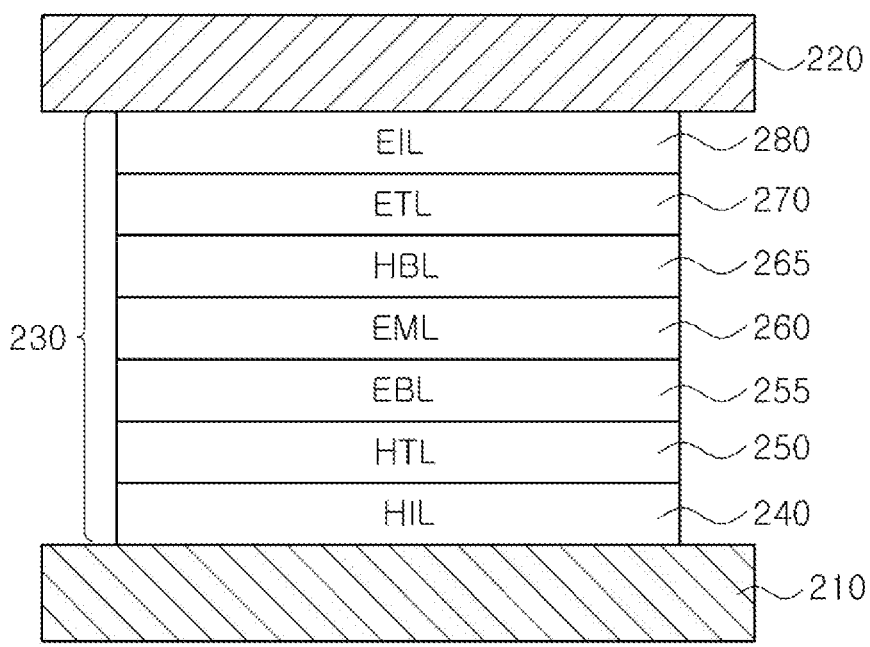
FIG. 4 is a cross-sectional view schematically showing an organic light-emitting diode in which an organic compound is applied to an organic light-emitting layer according to another exemplary embodiment of the present disclosure.

In addition, the organic light-emitting diode according to the present disclosure may further include one or more exciton blocking layers. FIG. 4 is a cross-sectional view schematically showing an organic light-emitting diode to which a phosphorescent compound is applied according to a second exemplary embodiment of the present disclosure. As shown in FIG. 4, an organic light-emitting diode 200 according to the second embodiment of the present disclosure includes a first electrode 210 and a second electrode 220 facing each other and an organic light-emitting layer 230 disposed between the first and second electrodes 210 and 220.

In one exemplary embodiment, the organic light-emitting layer 230 includes a hole injection layer 240, a hole transport layer 250, a light-emitting material layer 260, an electron transport layer 270, and an electron injection layer 280, which are sequentially stacked from the first electrode 210. In addition, the organic light-emitting layer 230 further includes an electron blocking layer (EBL) 255 as the first exciton blocking layer disposed between the hole transport layer 250 and the light-emitting material layer 260 and/or a hole blocking layer (HBL) 265 as the second exciton blocking layer disposed between the light-emitting material layer 260 and the electron transport layer 270.

As described above, the first electrode 210 may be an anode, and may be formed of a conductive material having a relatively large work function value such as ITO, IZO, ITZO, SnO, ZnO, ICO, and AZO. The second electrode 220 may be a cathode, and may be formed of a conductive material having a relatively small work function value such as Al, Mg, Ca, Ag, or alloys or combinations thereof.

The hole injection layer 240 is disposed between the first electrode 210 and a hole transport layer 250. The hole injection layer 240 is formed of any one of compounds such as MTDATA, CuPc, TCTA, NPB (NPD), HAT-CN, TDAPB, PEDOT/PSS and/or N-(biphenyl-4-yl)-9,9-dimethyl-N-(4-(9-phenyl-9H-carbazole-3-yl)phenyl)-9H-fluorene-2-amine.

The hole transport layer 250 is disposed between the first electrode 210 and the light-emitting material layer 260, and adjacent to the light-emitting material layer 260. The hole transport layer 250 may be composed of an aromatic amine compound such as TPD, NPD, CBP, N-(biphenyl-4-yl)-9,9-dimethyl-N-(4-(9-phenyl-9H-carbazole-3-yl)phenyl)-9H-fluorene-2-amine and/or N-(biphenyl-4-yl)-N-(4-(9-phenyl-9H-carbazole-3-yl)phenyl)biphenyl)-4-amine.

The light-emitting material layer 260 may be formed by doping a host with a dopant. For example, when the light-emitting material layer 260 is formed, about 1 to 30% by weight of the dopant may be added to the host, and the light-emitting material layer 260 may emit blue light. For example, the organic compounds represented by Formulas 1, 2 and Compounds 1 to 14 may be used as the host of the light-emitting material layer 260, and a compound exhibiting delayed fluorescence properties, for example, the compound represented by Formula 3 may be used as a dopant.

The electron transport layer 270 is disposed between the light-emitting material layer 260 and the electron injection layer 280. For example, the electron transport layer 270 may be derivatives of oxadiazole, triazole, phenanthroline, benzoxazole, benzothiazole, benzimidazole, triazine, and the like. For example, the electron transport layer 270 may be formed of Alq3, PBD, spiro-PBD, Liq, 2-[4-(9,10-di-2-naphthalenyl-2-anthracenyl)phenyl]-1-phenyl-1H-benzimidazole, BAlq, TAZ, Bphen, TPQ, and/or TPBi, without being limited thereto.

The electron injection layer 280 is disposed between the second electrode 220 and the electron transport layer 270. Examples of the materials of the electron injection layer 280 may include alkali halides such as LiF, CsF, NaF, and BaF2 and/or organometallic materials such as Liq, lithium benzoate, and sodium stearate, without being limited thereto.

Meanwhile, when holes move to the second electrode 220 through the light-emitting material layer 260 or electrons move to the first electrode 210 through the light-emitting material layer 260, the lifespan and efficiency of a device may be reduced. To prevent this, in the organic light-emitting diode 200 according to the second exemplary embodiment of the present disclosure, at least one exciton blocking layer is disposed adjacent to the light-emitting material layer 260.

For example, in the organic light-emitting diode 200 according to the second embodiment of the present disclosure, an electron blocking layer (EBL) 255 capable of controlling and preventing electron movement is disposed between the hole transport layer 250 and the light-emitting material layer 260.

For example, the electron blocking layer 255 may be formed of TCTA, tris[4-(diethylamino)phenyl]amine, N-(biphenyl-4-yl)-9,9-dimethyl-N-(4-(9-phenyl-9H-carbazole-3-yl)phenyl)-9H-fluorene-2-amine, tri-p-tolylamine, 1, 1-bis (4-(N,N'-di (ptolyl)amino)phenyl)cyclohexane (TAPC), MTDATA, 1,3-bis(N-carbazolyl)benzene (mCP), TPD, CuPC, N,N'-bis[4-[bis(3-methylphenyl)amino]phenyl]-N,N'-diphenyl-[1,1'-biphenyl]-4,4'-diamine (DNTPD) and/or TDAPB.

In addition, movement of holes between the light-emitting material layer 260 and the electron transport layer 270 is prevented by disposing a hole blocking layer 265 as the second exciton blocking layer between the light-emitting material layer 260 and the electron transport layer 270. In one exemplary embodiment, examples of the materials that may be used as the hole blocking layer at the electron transport layer 270 may include derivatives of oxadiazole, triazole, phenanthroline, benzoxazole, benzothiazole, benzimidazole, triazine, and the like.

For example, compared to the material used in the light-emitting material layer 260, the hole blocking layer 265 may be formed of a material having the lower highest occupied molecular orbital (HOMO) energy level such as 2,9-dimethyl-4,7-diphenyl-1,10-phenanthroline (BCP), BAlq, Alq3, PBD, spiro-PBD and/or Liq.

Since the organic light-emitting diode 200 according to the second embodiment of the present disclosure includes the light-emitting material layer 260 having delayed fluorescence properties, luminous efficacy may be improved. In addition, the light-emitting material layer 260 includes a host formed of an organic compound represented by Formula 1, 2 or Compounds 1 to 14.

Each of the organic compounds represented by Formulas 1, 2 and Compounds 1 to 14 is capable of functioning as an electron donor, and has an acridine moiety. When the acridine moiety combines with another moiety, distortion is increased, causing steric hindrance. Thus, the three-dimensional conformations of the organic compounds are limited and structurally robust. When the organic compounds represented by Formulas 1, 2 and Compounds 1 to 14 are used, excellent color purity may be secured, the lifespan of a device may be improved, and energy may be efficiently transferred to a dopant.

In addition, in the organic compound represented by Formula 1, since cyanide groups are connected to the acridine moiety, a triplet energy level is not lowered and a blue shift is facilitated. Therefore, when the organic compounds represented by Formulas 1, 2 and Compounds 1 to 14 are used, the organic light-emitting diode 200 having improved luminous efficacy, excellent color purity, and an increased element lifespan may be fabricated. In addition, since the organic light-emitting diode 200 according to the second embodiment of the present disclosure includes at least one exciton blocking layer (the exciton blocking layers 255 and 265), light emission is prevented at the interface between charge transport layers 250 and 270, adjacent to the light-emitting material layer 260, and thus the luminous efficacy and lifespan of the organic light-emitting diode 200 may be further improved.

Figure 5:
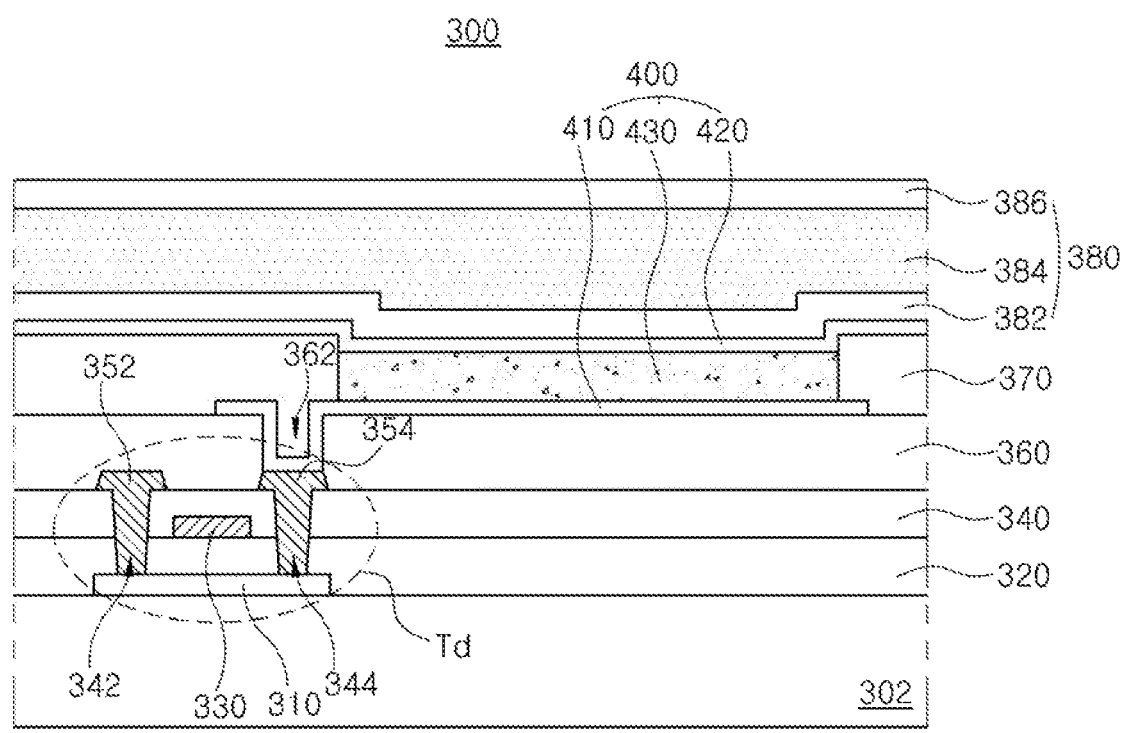
FIG. 5 is a cross-sectional view schematically showing an organic light-emitting diode display device as an example of an apparatus having an organic light-emitting diode in which an organic compound is applied to an organic light-emitting layer according to one exemplary embodiment of the present disclosure.

The organic light-emitting diode according to the present disclosure may be applied to an organic light-emitting diode display device or a lighting device. For example, a display device to which the organic light-emitting diode of the present disclosure is applied is described below. FIG. 5 is a schematic cross-sectional view showing the organic light-emitting diode display device according to an exemplary embodiment of the present disclosure.

As shown in FIG. 5, an organic light-emitting diode display device 300 includes a driving thin-film transistor (Td) as a driving element, a planarization layer 360 covering the driving thin-film transistor (Td), and an organic light-emitting diode 400 positioned on the planarization layer 360 and connected to the driving thin-film transistor (Td) which is a driving element. The driving thin-film transistor (Td) includes a semiconductor layer 310, a gate electrode 330, a source electrode 352, and a drain electrode 354. FIG. 3 shows a driving thin-film transistor (Td) having a coplanar structure.

A substrate 302 may be a glass substrate, a thin flexible substrate or a polymer plastic substrate. For example, the flexible substrate may be formed of any one of polyimide (PI), polyethersulfone (PES), polyethylene naphthalate (PEN), polyethylene terephthalate (PET), and polycarbonate (PC). The driving thin-film transistor (Td) as a driving element and the substrate 302 on which the organic light-emitting diode 400 is located constitute an array substrate.

The semiconductor layer 310 is formed on the substrate 302. For example, the semiconductor layer 310 may be formed of an oxide semiconductor material. In this case, a light shielding pattern and a buffer layer may be formed under the semiconductor layer 310. The light shielding pattern prevents light from being incident on the semiconductor layer 310, thereby preventing the semiconductor layer 310 from being degraded by light. Alternatively, the semiconductor layer 310 may be formed of polycrystalline silicon. In this case, impurities may be doped on both edges of the semiconductor layer 310.

A gate insulating film 320 made of an insulating material is formed on the semiconductor layer 310, and the gate insulating film 320 is formed on the entire surface of the substrate 302. The gate insulating film 320 may be formed of an inorganic insulating material such as silicon oxide ($SiO_2$) or silicon nitride ($SiN_x$).

The gate electrode 330 made of a conductive material such as a metal is formed on the gate insulating layer 320 at a central portion of the semiconductor layer 310. In addition, a gate line and a first capacitor electrode may be formed on the gate insulating film 320. The gate line may extend along a first direction, and the first capacitor electrode may be connected to the gate electrode 330. Meanwhile, the gate insulating film 320 formed on the entire surface of the substrate 302 may be patterned to have the same shape as the gate electrode 330.

An interlayer insulating film 340 made of an insulating material is formed on the entire surface of the substrate 302 and on the gate electrode 330. The interlayer insulating film 340 may be formed of an inorganic insulating material such as silicon oxide ($SiO_2$) or silicon nitride ($SiN_x$) or an organic insulating material such as benzocyclobutene or photo-acryl.

The interlayer insulating film 340 has a first semiconductor layer contact hole 342 and a second semiconductor layer contact hole 344, and both sides of the upper surface of the semiconductor layer 310 are exposed through the first and second semiconductor layer contact holes 342 and 344. The first and second semiconductor layer contact holes 342 and 344 are spaced apart from the gate electrode 330 at both sides of the gate electrode 330. Here, the first and second semiconductor layer contact holes 342 and 344 are also formed in the gate insulating film 320. Alternatively, when the gate insulating film 320 is patterned in the same shape as the gate electrode 330, the first and second semiconductor layer contact holes 342 and 344 are formed only in the interlayer insulating film 340.

The source electrode 352 and the drain electrode 354 made of conductive materials such as a metal are formed on the interlayer insulating film 340. In addition, a data line, a power line, and a second capacitor electrode extending along a second direction may be formed on the interlayer insulating film 340.

The source electrode 352 and the drain electrode 354 are spaced apart from each other around the gate electrode 330, and the electrodes 352 and 354 are respectively in contact with both sides of the semiconductor layer 310 through the first and second semiconductor layer contact holes 342 and 344. Although not shown, the data line extends along the second direction and intersects the gate line to define a pixel region, and the power line for supplying a high-potential voltage is located apart from the data line. The second capacitor electrode is connected to the drain electrode 354 and overlaps the first capacitor electrode, and the interlayer insulating layer 340 between the first and second capacitor electrodes is used as a dielectric layer to form a storage capacitor.

Meanwhile, the semiconductor layer 310, the gate electrode 330, the source electrode 352 and the drain electrode 354 constitute a driving thin-film transistor (Td). The driving thin-film transistor (Td) illustrated in FIG. 5 has a coplanar structure, in which the gate electrode 330, the source electrode 352, and the drain electrode 354 are disposed on the semiconductor layer 310. Alternatively, the driving thin-film transistor (Td) may have an inverted staggered structure, in which a gate electrode is located below a semiconductor layer and a source electrode and a drain electrode are located on the semiconductor layer. In this case, the semiconductor layer may be formed of amorphous silicon.

In addition, a switching thin-film transistor, a switching element, having substantially the same structure as the driving thin-film transistor (Td) is formed on the substrate 302. The gate electrode 330 of the driving thin-film transistor (Td) is connected to the drain electrode of the switching thin-film transistor, and the source electrode 352 of the driving thin-film transistor (Td) is connected to a power line. In addition, the gate electrode and the source electrode of the switching thin-film transistor are connected to a gate line and a data line, respectively.

In addition, the organic light-emitting diode display device 300 may include a color filter for absorbing light generated from the organic light-emitting diode 400. For example, the color filter may absorb red (R), green (G), blue (B), and white (W) light. In this case, red, green, and blue color filter patterns that absorb light may be formed separately for each pixel region, and each of these color filter patterns may be disposed so as to overlap an organic light-emitting layer 430 of the organic light-emitting diode 400 that emits light of a wavelength band to be absorbed. By adopting the color filter, the organic light-emitting diode display device 300 may realize full-color. For example, when the organic light-emitting diode display device 300 is a bottom-emission type, a color filter for absorbing light may be disposed on the interlayer insulating layer 340 corresponding to the organic light-emitting diode 400. In an alternative embodiment, when the organic light-emitting diode display device 300 is a top-emission type, the color filter may be located on the organic light-emitting diode 400, that is, on a second electrode 420.

The planarization layer 360 is formed on the entire surface of the substrate 302 and on the source electrode 352 and the drain electrode 354. The planarization layer 360 has a flat upper surface and a drain contact hole 362 through which the drain electrode 354 of the driving thin-film transistor (Td) is exposed. In FIG. 5, the drain contact hole 362 is formed directly on the second semiconductor layer contact hole 344, but may be formed apart from the second semiconductor layer contact hole 344.

The light-emitting diode 400 is disposed on the planarization layer 360, and includes a first electrode 410 connected to the drain electrode 354 of the driving thin-film transistor (Td) and the organic light-emitting layer 430 and the second electrode 420 sequentially stacked on the first electrode 410.

A first electrode 410 is formed separately for each pixel region. The first electrode 410 may be an anode, and may be formed of a conductive material having a relatively large work function value. For example, the first electrode 410 may be formed of a transparent conductive material such as ITO, IZO, ITZO, SnO, ZnO, ICO, and AZO.

Meanwhile, when the organic light-emitting diode display device 300 is a top-emission type, a reflective electrode or a reflective layer may be further formed under the first electrode 410. For example, the reflective electrode or the reflective layer may be formed of an aluminum-palladium-copper (APC) alloy.

In addition, a bank layer 370 covering an edge of the first electrode 410 is formed on the planarization layer 360. The bank layer 370 exposes the center of the first electrode 410 corresponding to the pixel region.

The organic light-emitting layer 430 is formed on the first electrode 410. In one exemplary embodiment, the organic light-emitting layer 430 may be a light-emitting material layer having a single layer structure. Alternatively, as shown in FIGS. 3 and 4, the organic light-emitting layer 430 may consist of several layers including a hole injection layer, a hole transport layer, an electron blocking layer, a light-emitting material layer, a hole blocking layer, an electron transport layer and/or an electron injection layer.

The second electrode 420 is formed on the substrate 302 on which the organic light-emitting layer 430 is formed. The second electrode 420 is disposed on the entire surface of a display region. Since the second electrode 420 is formed of a conductive material having a relatively low work function value, the second electrode 420 may be used as a cathode. For example, the second electrode 420 may be formed of any one of aluminum (Al), magnesium (Mg), calcium (Ca), silver (Ag), and alloys (e.g., aluminum-magnesium alloy (AlMg)) and combinations thereof.

An encapsulation film 380 is formed on the second electrode 420 to prevent external moisture from penetrating into the organic light-emitting diode 400. The encapsulation film 380 may have a structure in which a first inorganic insulating layer 382, an organic insulating layer 384, and a second inorganic insulating layer 386 are laminated, without being limited thereto.

As described above, since the organic light-emitting diode 400 has a dopant having delayed fluorescence properties disposed in the organic light-emitting layer 430, luminous efficacy is improved. In addition, the organic light-emitting layer 430 includes an organic compound represented by Formula 1, 2 or Compounds 1 to 14 as a host.

The three-dimensional conformations of the organic compounds represented by Formulas 1, 2 and Compounds 1 to 14 are limited and structurally robust. In addition, in organic compounds represented by Formulas 1, 2 and Compounds 1 to 14, since cyanide groups are connected to the acridine moiety, a triplet energy level is not lowered and a blue shift is facilitated. Therefore, when the organic compounds represented by Formulas 1, 2 and Compounds 1 to 14 are used, the color purity and the luminous efficacy of the organic light-emitting diode 400 to which the organic light-emitting layer 430 is applied and an organic light-emitting diode display device 300 may be improved, and an element lifespan may be increased.

Hereinafter, the present disclosure will be described in more detail with reference to the following examples. However, technical features of the present disclosure are not limited thereto.

Synthesis Example 1: Synthesis of Compound 1

1) Synthesis of Compound 1B

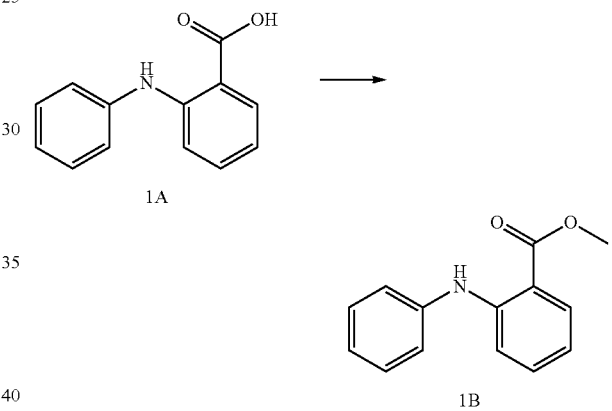

Compound 1A(4.52 g, 21.2 mmol) was mixed with a methanol solvent (100 ml) and then stirred under a nitrogen atmosphere. After further stirring at 0° C. for 10 minutes, 1 equivalent of thionyl chloride (21.2 mmol) was slowly added dropwise. The mixed solution was stirred at 90° C. for 12 hours or longer. After completion of the reaction, the solvent was removed, and distilled water and ethyl acetate were added to extract an organic layer. The moisture remaining in the extracted organic layer was removed using magnesium sulfate, followed by removal of the solvent, and then a crude product was subjected to wet purification using column chromatography using hexane and ethyl acetate to obtain a dark yellow liquid 1B(3.84 g, yield 80%).

2) Synthesis of Compound 1C

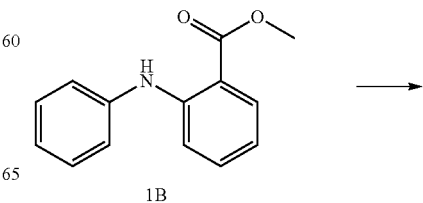

-continued

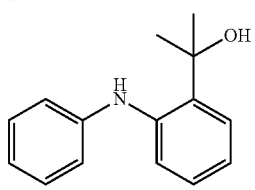

1C

Compound 1B (3.84 g, 16.91 mmol) was mixed with a tetrahydrofuran solvent (200 ml) and stirred under a nitrogen atmosphere. 4.6 equivalents of methylmagnesium bromide were slowly added dropwise. Reaction was carried out by stirring the mixture at room temperature for 12 hours or longer. After completion of the reaction, distilled water was slowly added, and an organic layer was extracted using ethyl acetate. The moisture remaining in the extracted organic layer was removed using magnesium sulfate, followed by removal of the solvent. Then, wet purification was performed using column chromatography using hexane and ethyl acetate to obtain a yellow liquid 1C (3.26 g, yield 85%).

3) Synthesis of Compound 1D

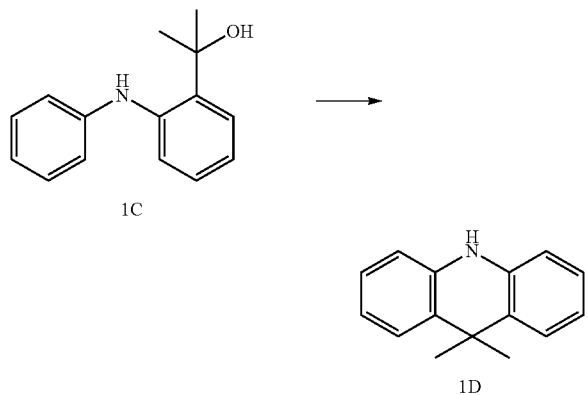

160 mL of an excess amount of phosphoric acid as a solvent was added to Compound 1C (3.26 g, 14.37 mmol), and the mixture was stirred at room temperature. After stirring for 16 hours or longer, 200 to 250 mL of distilled water was slowly added. Thereafter, the mixture was stirred for 0.5 to 1 hour, and a precipitated solid was filtered. An organic layer was extracted from the filtered solid using an aqueous sodium hydroxide solution and a dichloromethane solvent. The extracted organic layer was dehydrated using magnesium sulfate and the remaining organic solvent was removed to obtain a white solid 1D (2.7 g, yield 90%).

4) Synthesis of Compound 1E

-continued

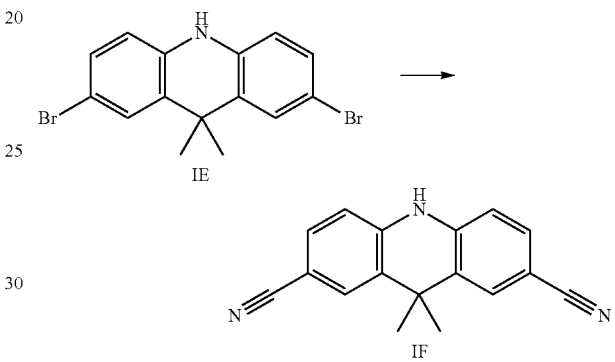

Under a nitrogen atmosphere (N₂ purging), Compound 1D (2.7 g, 12.93 mmol) was added to chloroform (200 ml), followed by stirring. After stirring, 3 equivalents of bromine were slowly added dropwise. After 8 hours, the reaction was quenched by addition of an aqueous sodium thiosulfate solution. Then, extraction was performed. Thereafter, purification was performed using a column using a developing solvent of methylenechloride (MC):hexane (1:5) to obtain a white solid 1E (4.24 g, yield 90%).

5) Synthesis of Compound 1F

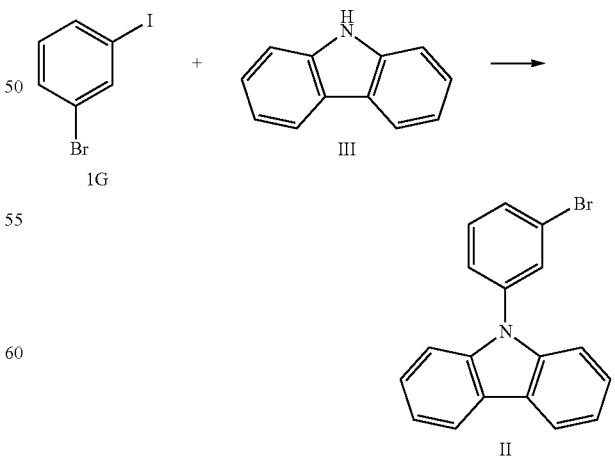

Under a nitrogen atmosphere (N₂ purging), Compound 1E (4.24 g, 11.63 mmol) and 2.3 equivalents of CuCN were added to DMF (200 ml), and stirred at 150° C. After 48 hours, the reaction mixture was slowly poured into ice water at 0° C., stirred for 30 minutes, and then an organic layer was extracted by addition of an aqueous ammonia solution. The solvent remaining in the organic layer was evaporated, and the organic material was adsorbed on silica. Then, purification using a column using a developing solvent of MC:hexane (1:1) was performed to obtain an ivory solid 1F (2.1 g, yield 70%).

6) Synthesis of Compound 11

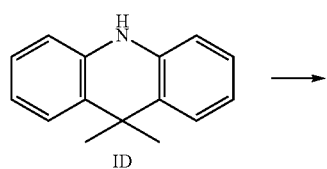

Under a nitrogen atmosphere (N₂ purging), Compound 1G (10 g, 35.48 mmol), 0.6 equivalent of Compound 1H, 0.1 equivalent of CuI, 3.5 equivalents of diaminocyclohexane, and 4.0 equivalents of potassium phosphate were added to 1,4-dioxane (350 ml), and stirred in a 90° C. oil bath. After 12 hours, water was added to the reaction mixture, and extraction was performed. Then, purification was performed using a column using a developing solvent of MC:hexane (5:1) to obtain a white solid 1I(7.97 g, yield 70%).

7) Synthesis of Compound 1

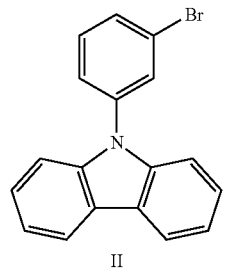

+

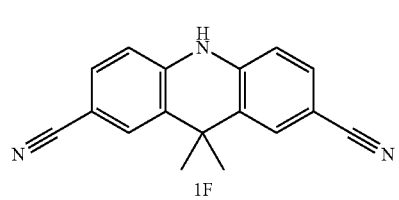

→

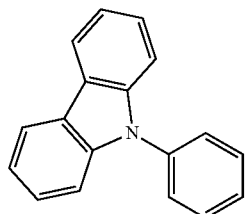

Compound 1

Under a nitrogen atmosphere (N₂ purging), Compound 1 42.96 g, 6.43 mmol), 1.2 equivalents of Compound 1F, 0.05 equivalent of tris(dibenzylideneacetone)dipalladium (0), 0.1 equivalent of triphenylphosphine, and 3.0 equivalents of sodium tert-butoxide were added to toluene (150 ml), and stirred in a 100° C. oil bath. After 10 hours, water was added to the reaction mixture, and extraction was performed. Then, purification was performed using a column using a developing solvent of hexane:MC (1:1) to obtain a white solid Compound 1(1.93 g, yield 60%).

Synthesis Example 2: Synthesis of Compound 2

1) Synthesis of Compound 2C

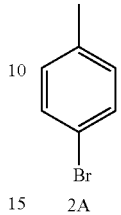 + 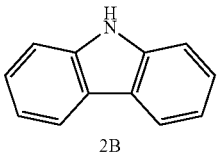 →

2A            2B

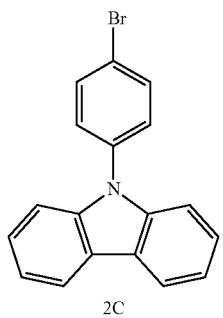

2C

Under a nitrogen atmosphere (N₂ purging), Compound 2A(10 g, 35.48 mmol), 0.6 equivalent of Compound 2B, 0.1 equivalent of CuI, 3.5 equivalents of diaminocyclohexane, and 4.0 equivalents of potassium phosphate were added to 1,4-dioxane (350 ml), and stirred in a 90° C. oil bath. After 12 hours, water was added to the reaction mixture, and extraction was performed. Then, purification was performed using a column using a developing solvent of MC:hexane (5:1) to obtain a white solid 2C (7.97 g, yield 70%).

2) Synthesis of Compound 2

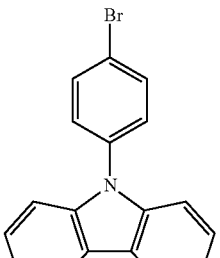

2C

+

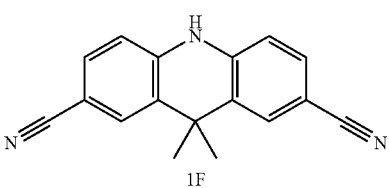

1F

→

-continued

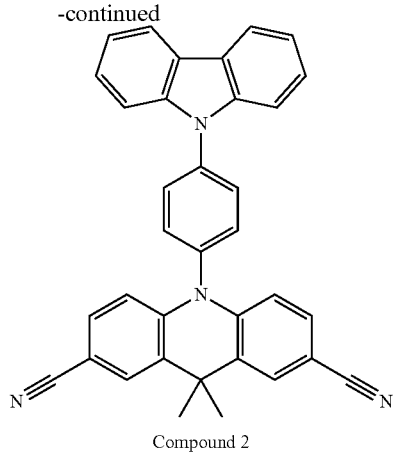

Compound 2

Under a nitrogen atmosphere (N₂ purging), Compound 2C (2.96 g, 6.43 mmol), 1.2 equivalents of Compound 1F, 0.05 equivalent of tris(dibenzylideneacetone)dipalladium(0), 0.1 equivalent of triphenylphosphine, and 3.0 equivalents of sodium tert-butoxide were added to toluene (150 ml), and stirred in a 100° C. oil bath. After 10 hours, water was added to the reaction mixture, and extraction was performed. Then, purification was performed using a column using a developing solvent of hexane:MC (1:1) to obtain a white solid Compound 2(2.1 g, yield 65%).

Synthesis Example 3: Synthesis of Compound 5

1) Synthesis of Compound 3B

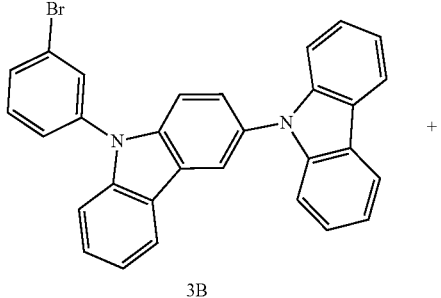

1G

3A

3B

Under a nitrogen atmosphere (N₂ purging), Compound 1G (10 g, 35.48 mmol), 0.6 equivalent of Compound 3A, 0.1 equivalent of CuI, 3.5 equivalents of diaminocyclohexane, and 4.0 equivalents of potassium phosphate were added to 1,4-dioxane (350 ml), and stirred in a 90° C. oil bath. After 15 hours, water was added to the reaction mixture, and extraction was performed. Then, purification was performed using a column using a developing solvent of hexane:MC (3:2) to obtain a white solid 3B(12.93 g. yield 75%).

2) Synthesis of Compound 5

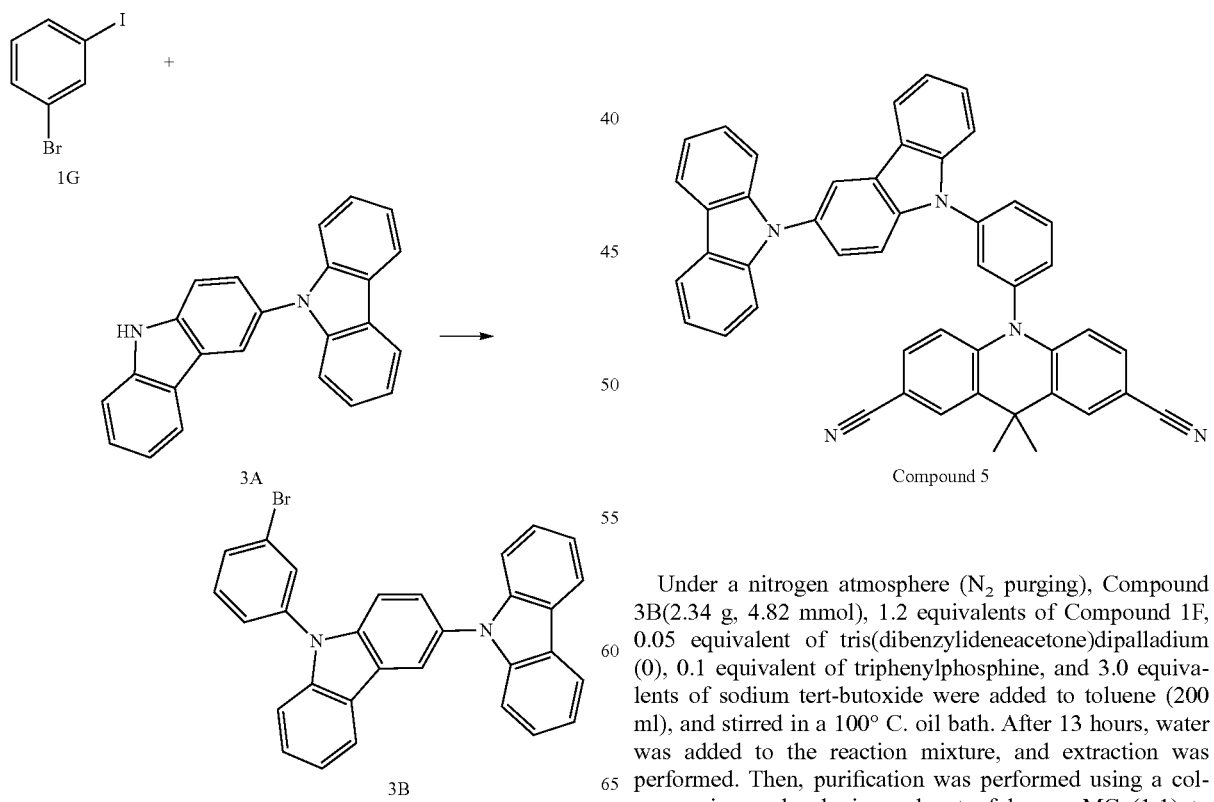

3B

1F

Compound 5

Under a nitrogen atmosphere (N₂ purging), Compound 3B(2.34 g, 4.82 mmol), 1.2 equivalents of Compound 1F, 0.05 equivalent of tris(dibenzylideneacetone)dipalladium (0), 0.1 equivalent of triphenylphosphine, and 3.0 equivalents of sodium tert-butoxide were added to toluene (200 ml), and stirred in a 100° C. oil bath. After 13 hours, water was added to the reaction mixture, and extraction was performed. Then, purification was performed using a column using a developing solvent of hexane:MC (1:1) to obtain a white solid Compound 5(1.6 g, yield 50%).

Synthesis Example 4: Synthesis of Compound 6

1) Synthesis of Compound 4B

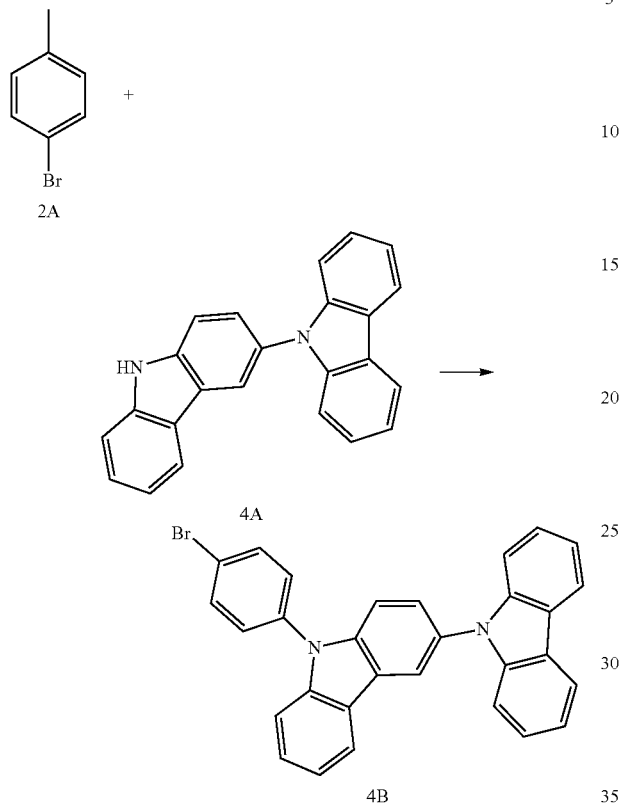

Under a nitrogen atmosphere (N₂ purging), Compound 2A(10 g, 35.48 mmol), 0.6 equivalent of Compound 4A, 0.1 equivalent of CuI, 3.5 equivalents of diaminocyclohexane, and 4.0 equivalents of potassium phosphate were added to 1,4-dioxane (350 ml), and stirred in a 90° C. oil bath. After 15 hours, water was added to the reaction mixture, and extraction was performed. Then, purification was performed using a column using a developing solvent of hexane:MC (3:2) to obtain a white solid 4B(12.07 g, yield 70%).

2) Synthesis of Compound 6

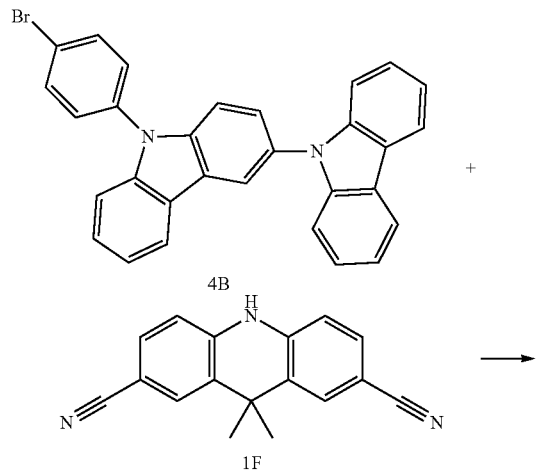

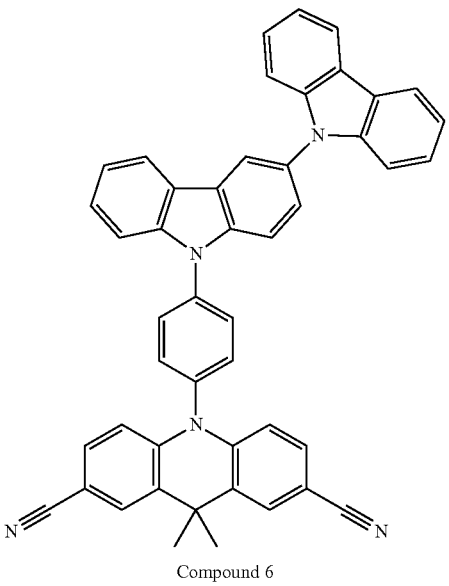

Compound 6

Under a nitrogen atmosphere (N₂ purging), Compound 4B(2.34 g, 4.82 mmol), 1.2 equivalents of Compound 1F, 0.05 equivalent of tris(dibenzylideneacetone)dipalladium (0), 0.1 equivalent of triphenylphosphine, and 3.0 equivalents of sodium tert-butoxide were added to toluene (150 ml), and stirred in a 100° C. oil bath. After 13 hours, water was added to the reaction mixture, and extraction was performed. Then, purification was performed using a column using a developing solvent of hexane:MC (1:1) to obtain a white solid Compound 6(1.76 g, yield 55%).

Example 1: Fabrication of Organic Light-Emitting Diode to which Compound 1 is Applied An organic light-emitting diode in which Compound 1 is used as the host of a light-emitting material layer was fabricated. First, a glass substrate with an ITO (with reflector) electrode of 40 mm×40 mm×0.5 mm (thickness) was ultrasonically cleaned with isopropyl alcohol, acetone and DI water for 5 minutes and then dried in an oven at 100° C. After cleaning, the substrate was treated with O₂ plasma for 2 minutes under vacuum, and the substrate was transferred to a deposition chamber to deposit other layers on top of the substrate. Organic layers were deposited by evaporation from a heated boat in the following order under a vacuum of about $10^{-7}$ Torr:

A hole injection layer (NPB, 40 Å), a hole transport layer (mCP, 10 Å), a light-emitting material layer (Compound 1 was used as a host, and 12 wt % of the material of Formula 3 was doped, 200 Å), an electron transport layer (TPBI, 300 Å), an electron injection layer (LiF), and a cathode (Al).

A capping layer (CPL) was formed and then encapsulated with glass. After the deposition process, the substrate was transferred from the deposition chamber into a drying box for film formation. Then, encapsulation was performed using a UV cured epoxy and a moisture getter.

Example 2: Fabrication of Organic Light-Emitting Diode to which Compound 2 is Applied The procedure of Example 1 was repeated except that Compound 2 instead of Compound 1 was used as the host of a light-emitting material layer to prepare an organic light-emitting diode.

Example 3: Fabrication of Organic Light-Emitting Diode to which Compound 5 is Applied The procedure of Example 1 was repeated except that Compound 5 instead of Compound 1 was used as the host of a light-emitting material layer to prepare an organic light-emitting diode.

Example 4: Fabrication of Organic Light-Emitting Diode to which Compound 6 is Applied The procedure of Example 1 was repeated except that Compound 6 instead of Compound 1 was used as the host of a light-emitting material layer to prepare an organic light-emitting diode.

Comparative Example: Fabrication of Organic Light-Emitting Diode

The procedure of Example 1 was repeated except that the material represented by Formula 4 below instead of Compound 1 was used as the host of a light-emitting material layer to prepare an organic light-emitting diode.

Formula 4

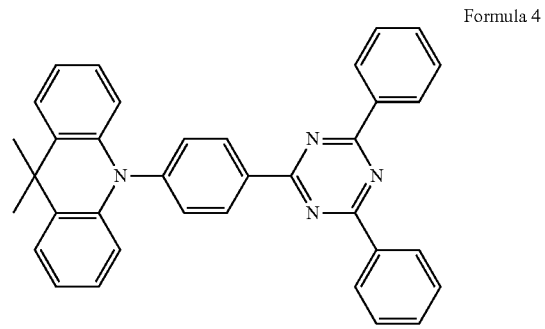 [SMILES: CC1(C)c2ccccc2N(c2ccc(-c3nc(-c4ccccc4)nc(-c4ccccc4)n3)cc2)c2ccccc21]

Experimental Example: Measurement of Luminescence Characteristics of Organic Light-Emitting Diode The properties of the organic light-emitting diodes fabricated according to Examples 1 to 4 and Comparative Example were measured. Each organic light-emitting diode having an emission area of 9 mm$^2$ was connected to an external power source, and a current source (KEITHLEY) and a photometer (PR 650) were used to evaluate the properties of the devices at room temperature. For the fabricated organic light-emitting diodes, current efficiency, power efficiency, external quantum efficiency (EQE), CIE color coordinates, and lifespan (T95) falling from 100% to 95% at a reference constant current of 1,000 nit luminance were measured. The obtained results are shown in Table 1.

TABLE 1

| Element | Current efficiency (cd/A) | Power efficiency (lm/W) | EQE (%) | CIE (X) | CIE (Y) | Lifespan (hr) (T95 @ 1,000 nit) |
|---|---|---|---|---|---|---|
| Example 1 | 9.5 | 8.1 | 10.3 | 0.130 | 0.082 | 5 |
| Example 2 | 10.1 | 7.6 | 10.7 | 0.141 | 0.099 | 4 |
| Example 3 | 11.7 | 9.0 | 12.4 | 0.149 | 0.112 | 9 |
| Example 4 | 12.4 | 9.8 | 13.1 | 0.152 | 0.121 | 10 |
| Comparative Example | 6.2 | 4.74 | 7.1 | 0.171 | 0.262 | 1.5 |

As shown in Table 1, when the organic compound synthesized according to the present disclosure is used as the host of a light-emitting material layer as compared with the case where the organic compound of Comparative Example is used as the host of a light-emitting material layer, current efficiency improved by up to 100%, power efficiency improved by up to 107%, external quantum efficiency improved by up to 85%, and the lifespan of the device increased 6.7-fold. In addition, based on the results of the color coordinate measurement, it was confirmed that when the organic compound of the present disclosure was used as a host, blue light having high color purity may be obtained. Therefore, when the organic compound of the present disclosure is applied to an organic light-emitting layer, an organic light-emitting diode having improved luminous efficacy, improved color purity, and an increased lifespan may be fabricated. Furthermore, an organic light-emitting diode, to which the organic compound of the present disclosure is applied, may be used for an organic light-emitting diode display device and/or a lighting device.

The organic compound of the present disclosure has an acridine moiety which is present in a distorted form when forming bonds with other moieties. The steric hindrance between the acridine moiety consisting of three hexagonal rings and an adjacent moiety is increased, and the three-dimensional conformation of the organic compound of the present disclosure is limited, so that the organic compound of the present disclosure has a rigid structure.

In addition, since the acridine moiety has cyanide groups (CNs) having excellent characteristics of electron withdrawing, the triplet energy of the organic compound is not lowered, and a blue shift is facilitated.

Therefore, when the organic compound of the present disclosure is used as the host of an organic light-emitting layer constituting an organic light-emitting diode and a compound having delayed fluorescence properties is used as a dopant, an organic light-emitting diode, an organic light-emitting diode display device, a lighting device, and the like, which can emit blue light of high purity and have increased luminous efficacy and an increased element lifespan, can be realized.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. An organic compound represented by Formula 1 below:

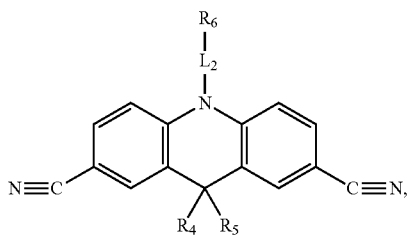

Formula 1 wherein each of $R_4$ and $R_5$ is independently selected from the group consisting of an unsubstituted C1 to C20 alkyl group, a substituted C1 to C20 alkyl group, an unsubstituted C5 to C30 aryl group, a substituted C5 to C30 aryl group, an unsubstituted C4 to C30 heteroaryl group, and a substituted C4 to C30 heteroaryl group,
$R_6$ is selected from the group consisting of an unsubstituted C5 to C30 aryl group, a substituted C5 to C30 aryl group, an unsubstituted C4 to C30 heteroaryl group, and a substituted C4 to C30 heteroaryl group, and
wherein $L_2$ is selected from the group consisting of an unsubstituted C5 to C10 arylene group, a substituted C5 to C10 arylene group consisting of one or two rings, an unsubstituted C4 to C30 heteroarylene group consisting of one or two rings, and a substituted C4 to C30 heteroarylene group consisting of one or two rings.

2. The organic compound according to claim 1, wherein the organic compound represented by Formula 1 is any one of compounds 1 to 14 below:

Compound 1

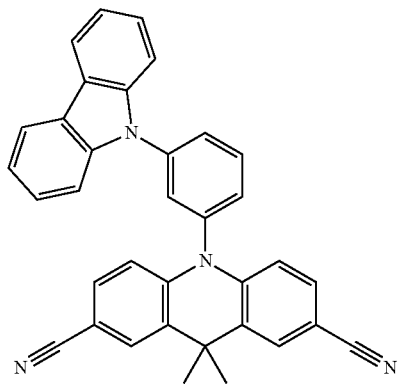

Compound 2

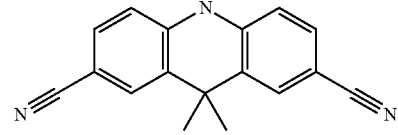

Compound 3

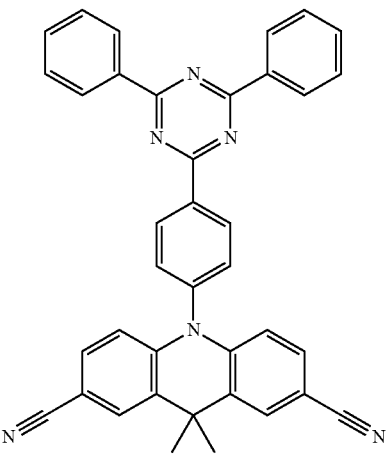

Compound 4

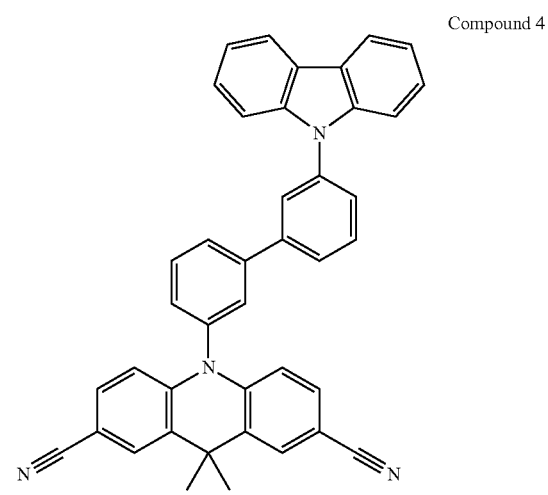

Compound 5

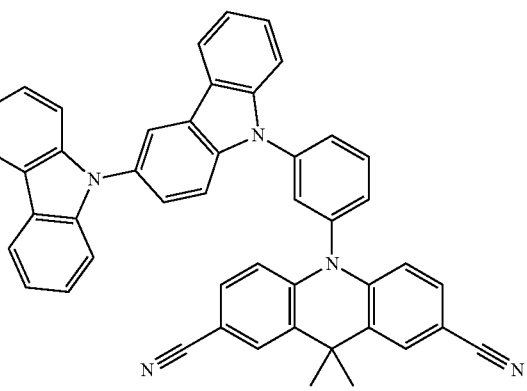

Compound 6
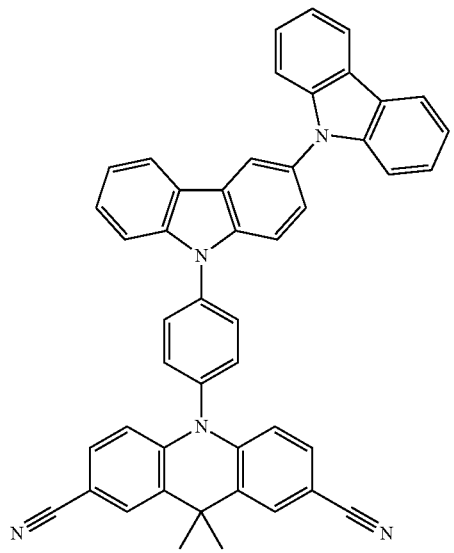
Compound 7
Compound 8
Compound 9
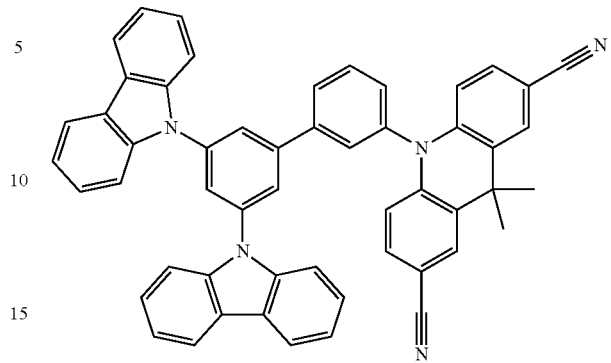
Compound 10
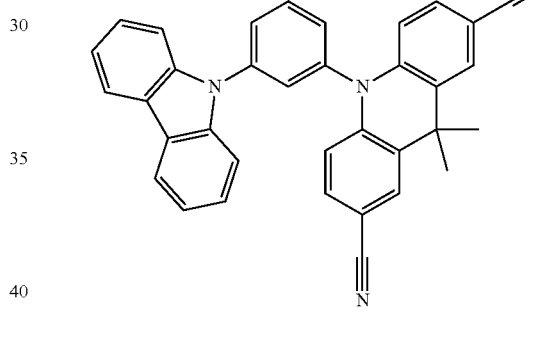
Compound 11
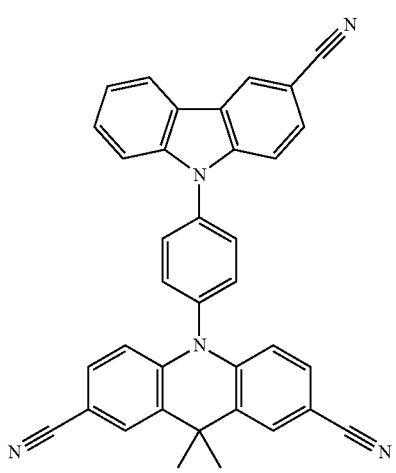

-continued

Compound 12

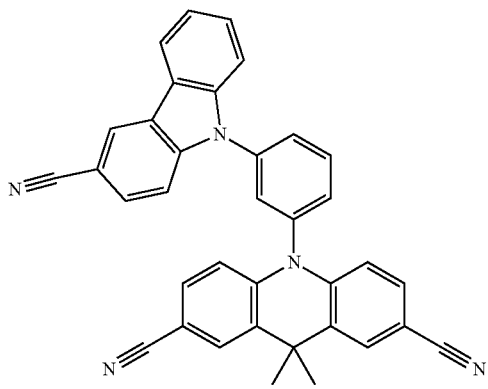

Compound 13

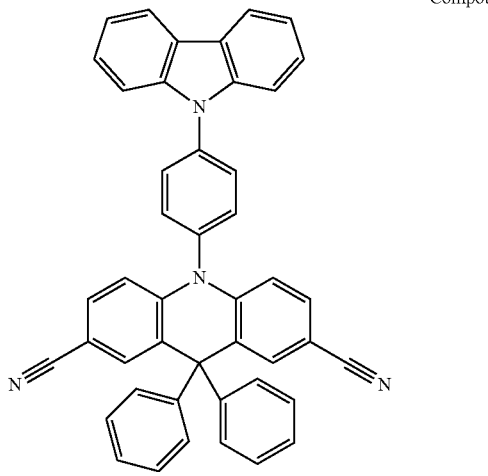

Compound 14

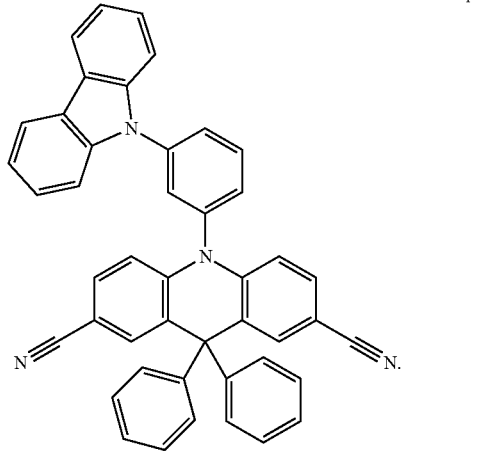

3. An organic light-emitting diode, comprising:
a first electrode and a second electrode facing each other; and
an organic light-emitting layer disposed between the first electrode and the second electrode, wherein the organic light-emitting layer comprises the organic compound according to claim 1.

4. The organic light-emitting diode according to claim 3, wherein the organic compound is suitable for use as a host of a light-emitting material layer.

5. The organic light-emitting diode according to claim 4, wherein the light-emitting material layer further comprises a dopant.

6. The organic light-emitting diode according to claim 5, wherein a difference ($|HOMO_{Host}-HOMO_{Dopant}|$) between a highest occupied molecular orbital energy level of the host ($HOMO_{Host}$) and a highest occupied molecular orbital energy level of the dopant ($HOMO_{Dopant}$) or a difference ($|LUMO_{Host}-LUMO_{Dopant}|$) between a lowest unoccupied molecular orbital energy level of the host ($LUMO_{Host}$) and a lowest unoccupied molecular orbital energy level of the dopant ($LUMO_{Dopant}$) is 0.5 eV or less.

7. The organic light-emitting diode according to claim 5, wherein a difference ($\Delta E_{ST}$) between a singlet energy level ($S_1$) of the dopant and a triplet energy level ($T_1$) of the dopant is 0.3 eV or less.

8. An organic light-emitting diode display device, comprising:
a substrate;
the organic light-emitting diode according to claim 3 and disposed on the substrate; and
a driving element disposed on the substrate and connected to a first electrode of the organic light-emitting diode.

9. The organic light-emitting diode display device according to claim 8, wherein the organic compound is suitable for use as a host of a light-emitting material layer.

10. The organic light-emitting diode display device according to claim 9, wherein the light-emitting material layer further comprises a dopant.

11. The organic light-emitting diode display device according to claim 10, wherein a difference ($|HOMO_{Host}-HOMO_{Dopant}|$) between a highest occupied molecular orbital energy level of the host ($HOMO_{Host}$) and a highest occupied molecular orbital energy level of the dopant ($HOMO_{Dopant}$) or a difference ($|LUMO_{Host}-LUMO_{Dopant}|$) between a lowest unoccupied molecular orbital energy level of the host ($LUMO_{Host}$) and a lowest unoccupied molecular orbital energy level of the dopant ($LUMO_{Dopant}$) is 0.5 eV or less.

12. The organic light-emitting diode display device according to claim 10, wherein a difference ($\Delta E_{ST}$) between a singlet energy level ($S_1$) of the dopant and a triplet energy level ($T_1$) of the dopant is 0.3 eV or less.

13. The organic light-emitting diode according to claim 3, wherein the organic compound is any one of compounds 1 to 14 below:

Compound 1

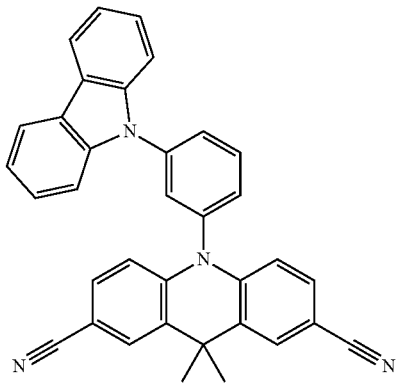

-continued
Compound 2
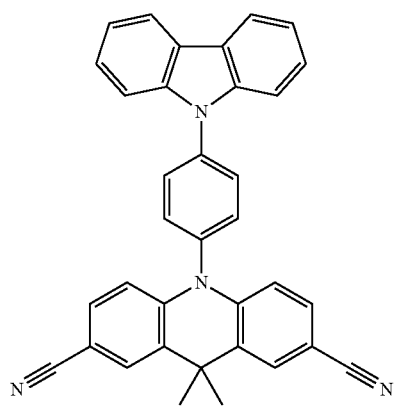
Compound 3
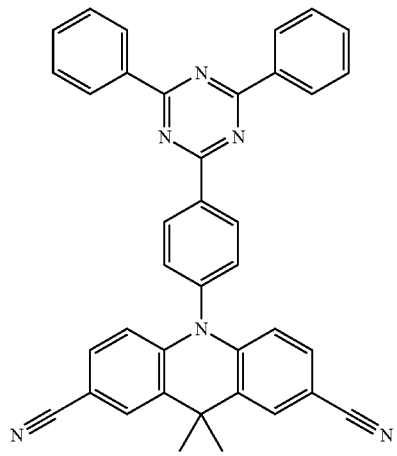
Compound 4
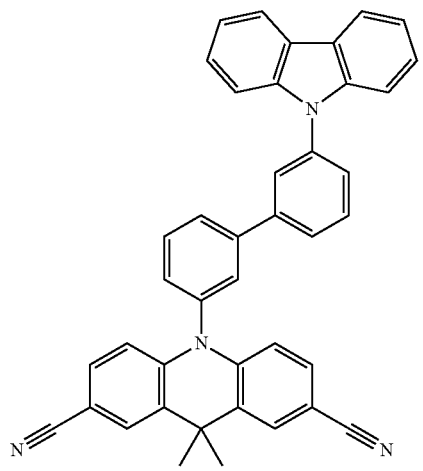
-continued
Compound 5
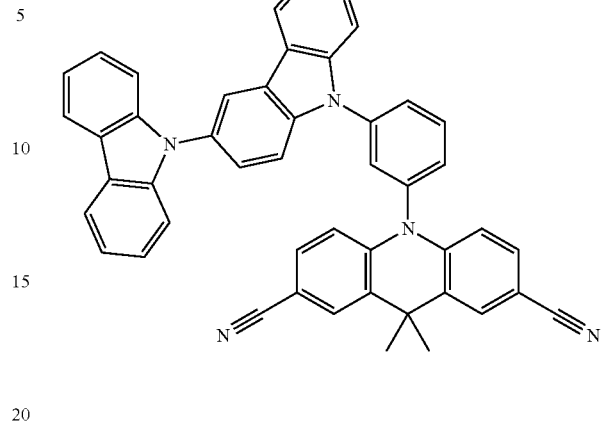
Compound 6
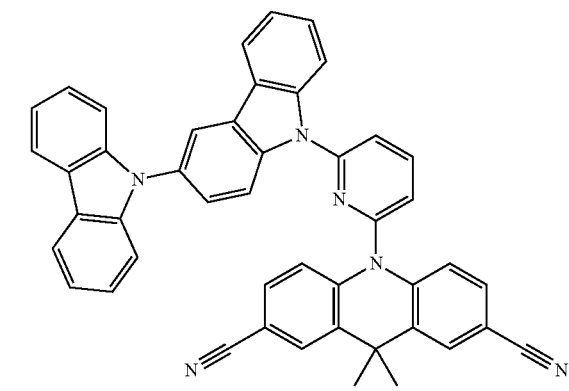
Compound 7

-continued
Compound 8
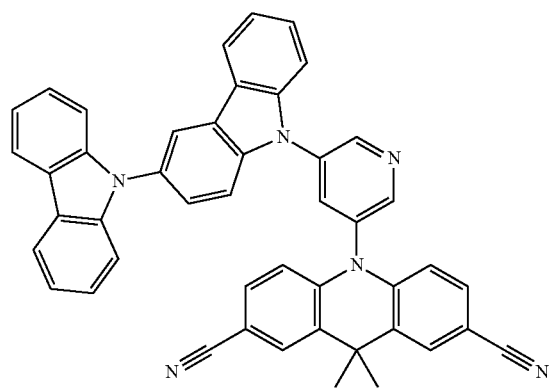
Compound 9
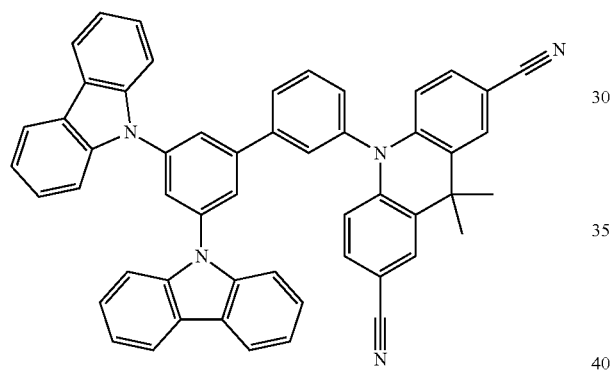
Compound 10
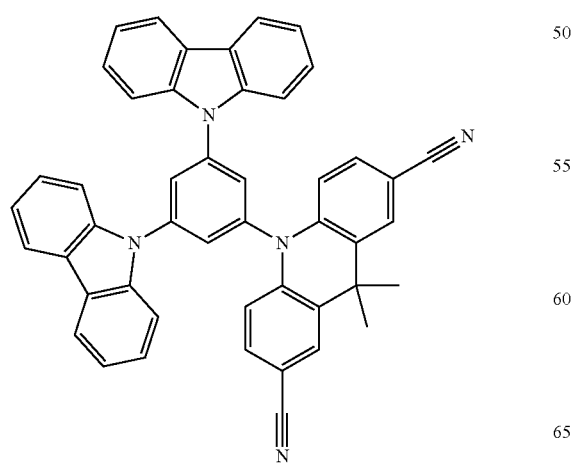
-continued
Compound 11
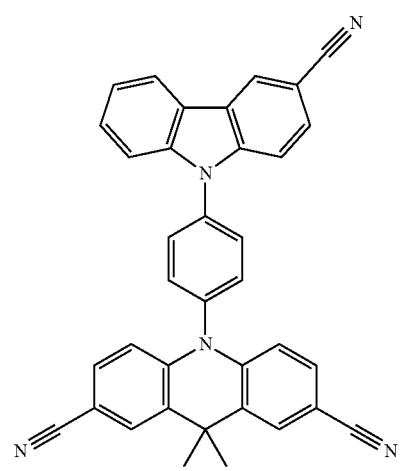
Compound 12
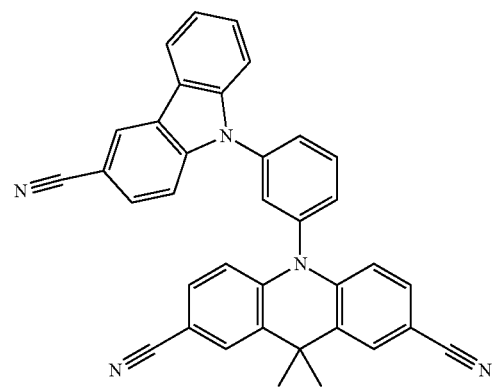
Compound 13
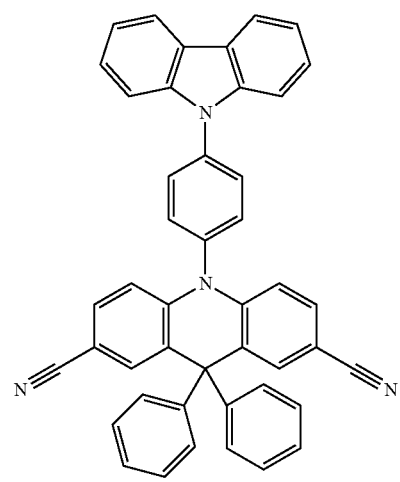

Compound 14
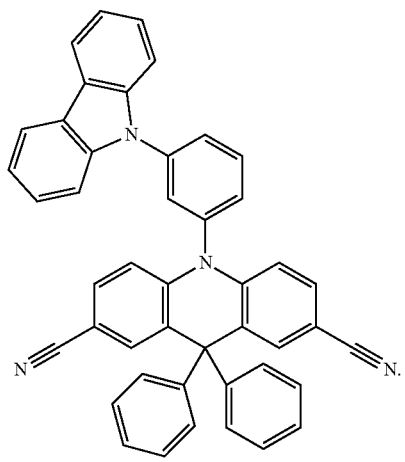
14. The organic light-emitting diode display device according to claim 8, wherein the organic compound is any one of compounds 1 to 14 below:
Compound 1
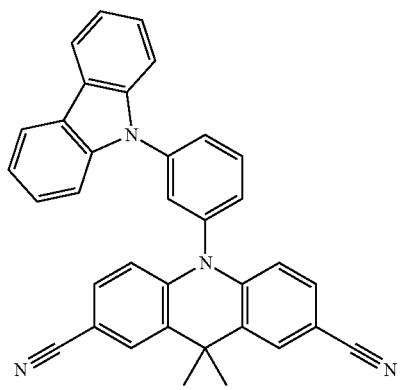
Compound 2
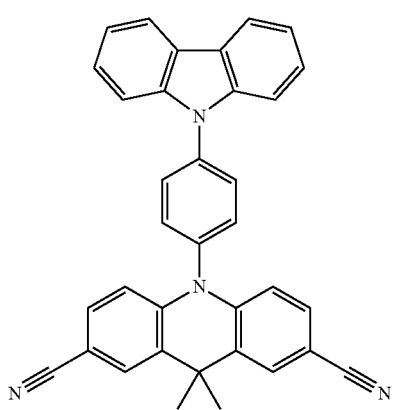
Compound 3
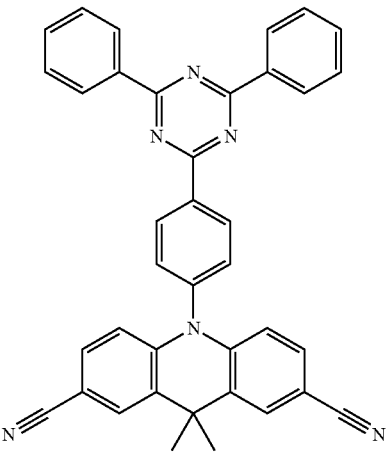
Compound 4
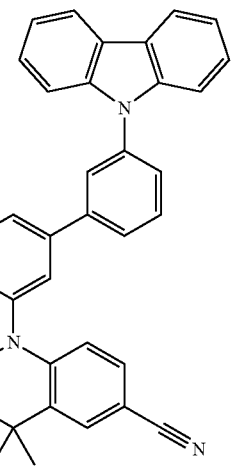
Compound 5
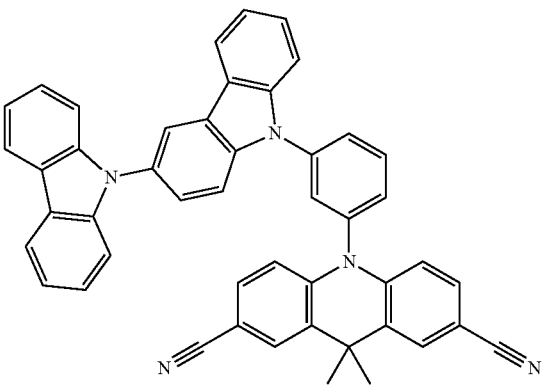

Compound 6
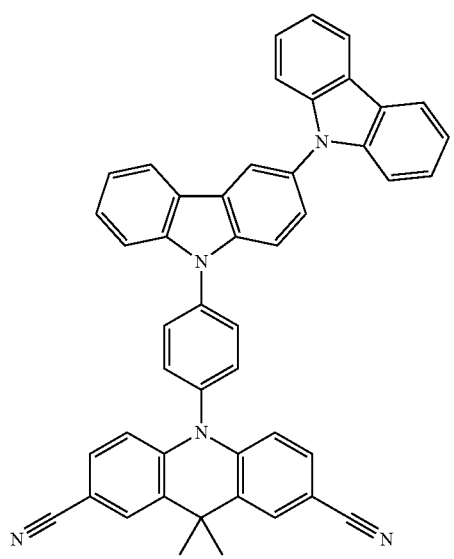
Compound 7
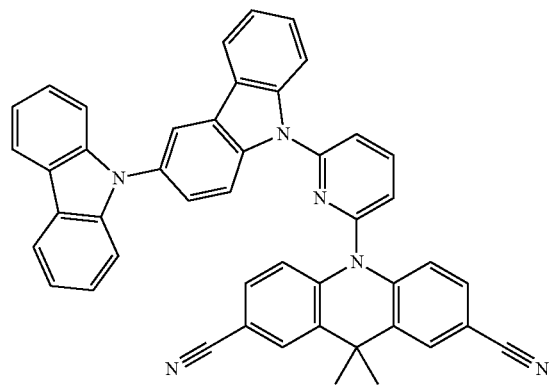
Compound 8
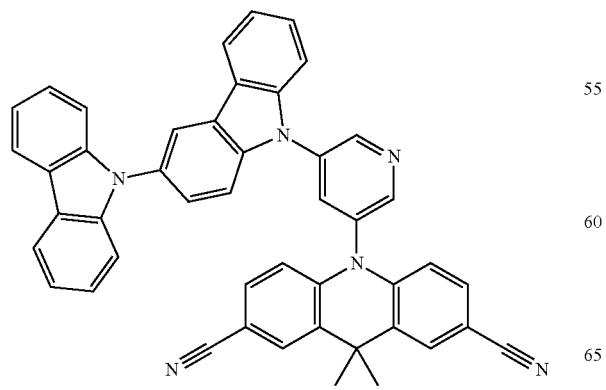
Compound 9
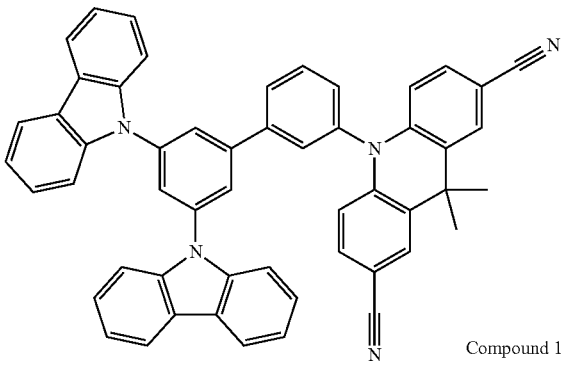
Compound 10
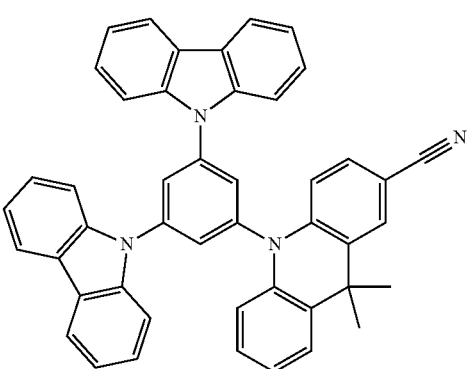
Compound 11
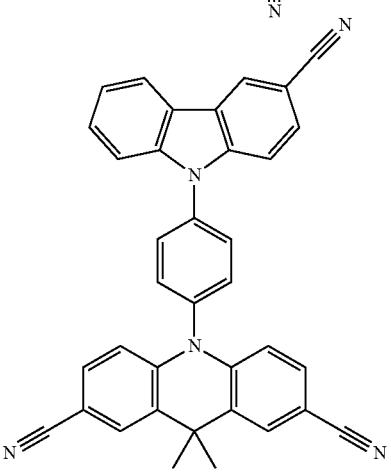
Compound 12
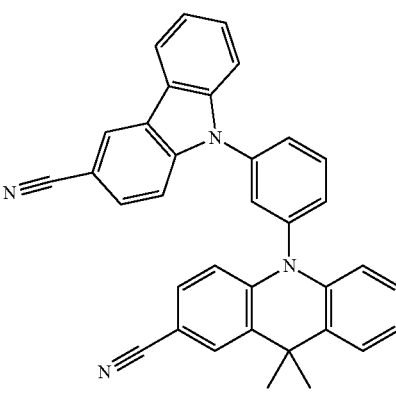

Compound 13
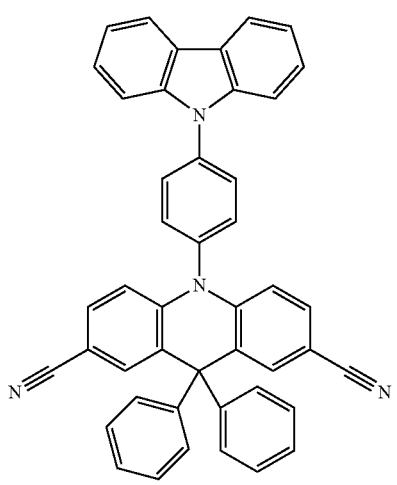
Compound 14
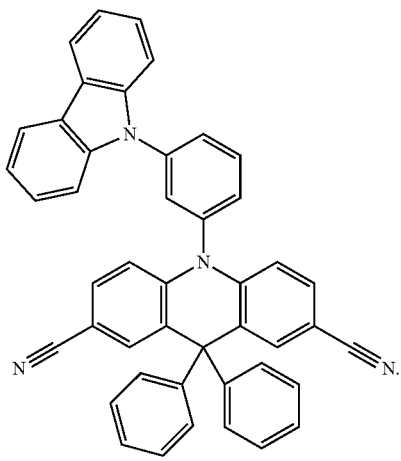
* * * * *